(12) United States Patent
Ozaki et al.

(10) Patent No.: US 10,087,428 B2
(45) Date of Patent: Oct. 2, 2018

(54) ACYL-ACP THIOESTERASE

(71) Applicant: Kao Corporation, Chuo-ku, Tokyo (JP)

(72) Inventors: Tatsuro Ozaki, Wakayama (JP);
Hiroyuki Ohta, Yokohama (JP); Koichi Hori, Machida (JP)

(73) Assignee: KAO CORPORATION, Tokyo (JP)

( * ) Notice: Subject to any disclaimer, the term of this patent is extended or adjusted under 35 U.S.C. 154(b) by 100 days.

(21) Appl. No.: 14/646,895

(22) PCT Filed: Dec. 20, 2013

(86) PCT No.: PCT/JP2013/084244
§ 371 (c)(1),
(2) Date: May 22, 2015

(87) PCT Pub. No.: WO2014/103930
PCT Pub. Date: Jul. 3, 2014

(65) Prior Publication Data
US 2015/0307860 A1    Oct. 29, 2015

(30) Foreign Application Priority Data
Dec. 27, 2012  (JP) .................. 2012-286058

(51) Int. Cl.
| C12P 7/64 | (2006.01) |
| C12N 1/00 | (2006.01) |
| C12N 1/13 | (2006.01) |
| C12N 1/21 | (2006.01) |
| C12N 9/16 | (2006.01) |

(52) U.S. Cl.
CPC .............. *C12N 9/16* (2013.01); *C12P 7/6409* (2013.01); *C12Y 301/02014* (2013.01)

(58) Field of Classification Search
CPC . C12N 9/12; C12N 9/16; C12P 7/6409; C12P 7/6463; C12Y 301/02014
See application file for complete search history.

(56) References Cited

U.S. PATENT DOCUMENTS

| 2009/0317878 A1 | 12/2009 | Champagne et al. |
| 2011/0217743 A1 | 9/2011 | Yoshida et al. |
| 2015/0111264 A1 | 4/2015 | Ozaki et al. |
| 2016/0130615 A1 | 5/2016 | Ozaki |
| 2017/0044580 A1 | 2/2017 | Sugihara et al. |
| 2017/0107545 A1 | 4/2017 | Tojo et al. |
| 2017/0114376 A1 | 4/2017 | Ozaki et al. |

FOREIGN PATENT DOCUMENTS

| JP | 07-501924 A | 3/1995 |
| JP | 11-505115 A | 5/1999 |
| JP | 2002-502263 A | 1/2002 |
| JP | 2014-132892 A | 7/2014 |
| JP | 2015-177771 A | 10/2015 |
| WO | WO 92/20236 A1 | 11/1992 |
| WO | WO 96/36719 A1 | 11/1996 |
| WO | WO 98/55633 A1 | 12/1998 |
| WO | WO 2011/108755 A1 | 9/2011 |
| WO | WO 2011/150410 A2 | 12/2011 |
| WO | WO 2012/061647 A2 | 5/2012 |
| WO | WO 2012/087673 A1 | 6/2012 |
| WO | WO 2015/005139 A1 | 1/2015 |
| WO | WO 2015/133305 A1 | 9/2015 |
| WO | WO 2015/194628 A1 | 12/2015 |
| WO | WO 2016/021481 A1 | 2/2016 |
| WO | WO 2016/076231 A1 | 5/2016 |
| WO | WO 2016/088511 A1 | 6/2016 |

OTHER PUBLICATIONS

International Search Report (ISR) for PCT/JP2013/084244; I.A. fd: Dec. 20, 2013, dated Feb. 18, 2014, the Japanese Patent Office, Tokyo, Japan.

International Preliminary Report on Patentability (IPRP) including the Written Opinion of the International Searching Authority (PCT Rule 44bis) for PCT/JP2013/084244; I.A. fd: Dec. 20, 2013, dated Jun. 30, 2015, by the International Bureau of WIPO, Geneva, Switzerland.

GenBank Accession No. EKU23063.1, Thioesterase superfamily member 4 [Nannochloropsis gaditana CCMP526], Radakovits, R. et al., direct submission, GenBank version EKU23063.1, GI:422295764, PLN Nov. 20, 2012, retrieved from the Internet, www.ncbi.nlm.nih.gov/protein/EKU23063.1?report=girevhist>, on Feb. 3, 2014.

GenBank Accession No. EKU23063.1, Thioesterase superfamily member 4 [Nannochloropsis gaditana CCMP526], Radakovits, R. et al., direct submission, GenBank version EKU23063.1, GI:422295764, PLN Nov. 20, 2012, last update Mar. 18, 2015, retrieved from the Internet, www.ncbi.nlm.nih.gov/protein/EKU23063.1?report=girevhist>, on Apr. 23, 2015.

Radakovits, R. et al., "Draft genome sequence and genetic transformation of the oleaginous alga *Nannochloropsis gaditana*," Nature Communications (Feb. 21, 2012), vol. 3, Article No. 686, ten pages (1-10), doi:10.1038/ncomms1688; and Corrigendum to correct the Title, Nature Communications vol. 4, Article No. 2356, Sep. 19, 2013; Nature Pub. Group, London, England).

Gong, Y et al., "Characterization of a novel thioesterase (PtTE) from *Phaeodactylum tricornutum*," J Basic Microbiol, Dec. 2011; 51(6): 666-672, Wiley-VCH Verlag, Weinheim, Germany.

Radakovits, R et al., "Genetic Engineering of Algae for Enhanced Biofuel Production," Eukaryot Cell, Apr. 2010; 9:486-501, American Society for Microbiology, Washington, DC.

(Continued)

*Primary Examiner* — Maryam Monshipouri
(74) *Attorney, Agent, or Firm* — Sterne, Kessler, Goldstein & Fox P.L.L.C.

(57) ABSTRACT

An acyl-ACP thioesterase consisting of an amino acid sequence of the $115^{th}$ to $274^{th}$ amino acids set forth in SEQ ID NO: 1; an acyl-ACP thioesterase gene encoding the protein; a transformant having the gene; and a method of producing a lipid using the transformant.

16 Claims, No Drawings
Specification includes a Sequence Listing.

(56) References Cited

OTHER PUBLICATIONS

Voelker, TA et al., "Fatty acid biosynthesis redirected to medium chains in transgenic oilseed plants," Science, Jul. 1992; 257:72-74, American Assoc Adv Sci, Washington, DC.
Excerpted file history, U.S. Appl. No. 14/897,049, § 371 Date: Dec. 19, 2015, Notice of Allowance and Fees Due dated Aug. 15, 2017: Examiner initiated interview summary (mail room date Aug. 4, 2017); Office Action Appendices (mail room date Aug. 4, 2017); and Statement of Common Ownership (Misc incoming letter mail room date Aug. 4, 2017) the United States Patent and Trademark Office, Alexandria, VA.
Jones, A et al., "Palmitoyl-acyl carrier protein (ACP) thioesterase and the evolutionary origin of plant acyl-ACP thioesterases," Plant Cell. Mar. 1995;7(3):359-71, American Society of Plant Physiologists, Rockville, MD.
Serrano-Vega, MJ et al., "Cloning, characterization and structural model of a FatA-type thioesterase from sunflower seeds (*Helianthus annuus* L.)," Planta. Aug. 2005;221(6):868-80. Epub Apr. 20, 2005, Springer-Verlag, NY.
Lipman, DJ et al., "Rapid and sensitive protein similarity searches," Science. Mar. 22, 1985;227(4693):1435-41, Am. Assoc. Adv. Sci. Washington, DC.
Pearson, WR et al., "Improved tools for biological sequence comparison," Proc Nati Acad Sci U S A. Apr. 1988;85(8):2444-8, Nat. Acad. Sci, Washington, DC.
Lambert, C, "Review of common sequence alignment methods: Clues to enhance reliability," Current Genomics, 2003, 4:131-146, Bentham Science Publishers, Hilversum, Netherlands.
Excerpted file history, U.S. Appl. No. 15/520,146, § 371 Date: Apr. 19, 2017, Preliminary amendment filed Apr. 19, 2017, the United States Patent and Trademark Office, Alexandria, VA.
Excerpted file history, U.S. Appl. No. 15/520,138, § 371 Date: Apr. 19, 2017, Preliminary amendment filed Apr. 19, 2017, the United States Patent and Trademark Office, Alexandria, VA.
Excerpted file history, U.S. Appl. No. 14/897,049, § 371 Date: Dec. 9, 2015, restriction requirement mailed Jan. 23, 2017 and Applicant's preliminary amendment filed Dec. 9, 2015, the United States Patent and Trademark Office, Alexandria, VA.
Excerpted file history, U.S. Appl. No. 14/897,049, § 371 Date: Dec. 9, 2015, applicant's amendment and reply filed Jul. 12, 2017, non-final office action dated Mar. 15, 2017, applicant's reply to the Jan. 23, 2017 restriction requirement filed Feb. 24, 2017, United States Patent and Trademark Office, Alexandria, VA.
Mayer, KM et al., "Identification of amino acid residues involved in substrate specificity of plant acyl-ACP thioesterases using a bioinformatics-guided approach," BMC Plant Biol. Jan. 3, 2007;7:1, DOI: 10.1186/1471-2229-7-1, 11 pages, BioMed Central, London, England.
Nannochloropsis gaditana strain B-31 contig00219, whole genome shotgun sequence, [online], Feb. 14, 2014, database GenBank, AZIL01000370, protein id : EWM27855.1, [retrieval date Aug. 19, 2015], Internet<URL:http://www.ncbi.nlm.nih.gov/nuccore/AZIL01000370.
Tojo, T. et al., "Kokoyashi Yurai Acyl-ACP Thioesterase wa Chusa Shibosan no Seisan ni Kan' yo suru," ("Characterization of Acyl-ACP thioesterase derived from coconut"), [online], 2012, Japan Society for Bioscience, Biotechnology, and Agrochemistry 2012 Nendo Taikai Topic Sho Happyo Bango: 2C10a02, [retrieval date Aug. 20, 2015 (Aug. 20, 2015) ], Internet<URL: http://www.jsbba.or.jp/wp-content/uploads/file/award/2012/topics/7_2C10a02.pdf, Dynacom Co., Ltd.
Yuan, L et al., "The catalytic cysteine and histidine in the plant acyl-acyl carrier protein thioesterases," J Biol Chem. Feb. 16, 1996;271(7):3417-3419, American Society for Biochemistry and Molecular Biology, Baltimore, MD.
Yuan, L et al., "Modification of the substrate specificity of an acyl-acyl carrier protein thioesterase by protein engineering," Proc Natl. Acad Sci U S A. Nov. 7, 1995;92(23):10639-10643, National Academy of Sciences, Washington, DC.
Zhang, H. et al., "Proof that Dinoflagellate Spliced Leader (DinoSL) is a Useful Hook for Fishing Dinoflagellate Transcripts from Mixed Microbial Samples: *Symbiodinium kawagutii* as a Case Study," Protist 164:510-527 (Jul. 2013; Epub: Jun. 14, 2013), Elsevier GmbH.
Zhang, X et al., "Efficient free fatty acid production in *Escherichia coli* using plant acyl-ACP thioesterases," Metabolic Engineering 13 (2011) 713-722, Brugge, Belgium.
PCT phase of U.S. Appl. No. 14/897,049—International Search Report (ISR) for PCT/JP2014/067137; I.A. fd: Jun. 27, 2014, dated Sep. 2, 2014, from the Japanese Patent Office, Tokyo, Japan.
PCT phase of U.S. Appl. No. 14/897,049—International Preliminary Report on Patentability (IPRP), Chapter 1 of the Patent Cooperation Treaty, including the Written Opinion for PCT/JP2014/067137; I.A. fd: Jun. 27, 2014, dated Jan. 12, 2016, from the International Bureau of WIPO, Geneva, Switzerland.
PCT Phase of U.S. Appl. No. 15/317,345—International Search Report (ISR) for PCT/JP2015/067581; I.A. fd Jun. 18, 2015, dated Sep. 1, 2015 from the Japan Patent Office, Tokyo, Japan.
PCT Phase of U.S. Appl. No. 15/317,345—International Preliminary Report on Patentability (IPRP), Chapter I of the Patent Cooperation Treaty, including the Written Opinion for PCT/JP2015/067581; I.A. fd Jun. 18, 2015, dated Dec. 20, 2016, by the International Bureau of WIPO, Geneva, Switzerland.
Leggat, W. et al., "Analysis of an EST library from the dinoflagellate (*Symbiodinium* sp.) symbiont of reef-building corals," Journal of Phycology 43(5): 1010-1021, Oct. 2007, Wiley.
Excerpted file history, U.S. Appl. No. 15/317,345, § 371 dated Dec. 8, 2016, preliminary amendment filed Dec. 8, 2016, the United States Patent and Trademark Office, Alexandria, VA.
GenBank Database Accession No. AY835984 version AY835984.1, "Diploknema butyracea chloroplast palmitoyl/oleoyl specific acyl-acyl carrier protein thioesterase precursor (FatB) mRNA, partial cds; nuclear gene for chloroplast product," printed from wvvw.ncbi.nlm.nih.gov/nuccore/61661996?sat=4&satkey=45297464, dated Mar. 13, 2017.
Sang, H., "Prospects for transgenesis in the chick," Mech Dev. Sep. 2004;121(9):1179-1186, Elsevier, Elsevier Ireland Ltd.
PCT Phase of U.S. Appl. No. 15/111,635—International Search Report (ISR) for PCT/JP2015/054960; I.A. fd Feb. 23, 2015, dated May 26, 2015 from the Japan Patent Office, Tokyo, Japan.
PCT Phase of U.S. Appl. No. 15/111,635—International Preliminary Report on Patentability (IPRP), Chapter I of the Patent Cooperation Treaty, including the Written Opinion for PCT/JP2015/0054960; I.A. fd Feb. 23, 2015, dated Sep. 6, 2016, by the International Bureau of WIPO, Geneva, Switzerland.
PCT Phase of U.S. Appl. No. 15/317,347—International Search Report (ISR) for PCT/JP2015/071666; I.A. fd Jul. 30, 2015, dated Oct. 13, 2015 from the Japan Patent Office, Tokyo, Japan.
PCT Phase of U.S. Appl. No. 15/111,635—International Preliminary Report on Patentability (IPRP), Chapter I of the Patent Cooperation Treaty, including the Written Opinion for PCT/JP2015/071666; I.A. fd Jul. 30, 2015, dated Feb. 7, 2017, by the International Bureau of WIPO, Geneva, Switzerland.
Excerpted file history, U.S. Appl. No. 15/110,635, § 371 dated Jul. 8, 2016, preliminary amendment filed Sep. 26, 2016 and preliminary amendment filed Jul. 8, 2016, the United States Patent and Trademark Office, Alexandria, VA.
Excerpted file history, U.S. Appl. No. 15/317,347, § 371 dated Dec. 8, 2016, preliminary amendment filed Dec. 8, 2016, the United States Patent and Trademark Office, Alexandria, VA.

SEQUENCE LISTING

<160> NUMBER OF SEQ ID NOS: 60

<210> SEQ ID NO 1
<211> LENGTH: 274
<212> TYPE: PRT
<213> ORGANISM: Nannochloropsis gaditana CCMP526

<400> SEQUENCE: 1

```
Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
            260                 265                 270

Ile Ser
```

<210> SEQ ID NO 2
<211> LENGTH: 825
<212> TYPE: DNA
<213> ORGANISM: Nannochloropsis gaditana CCMP526

<400> SEQUENCE: 2

```
atgctatgtt gcgcctgtaa atcagtgcat gcgactatta gtgtcgcctt tattggtact      60
cggaagccac atcgtttgcc tgcattgttt ccattgttcc ttgccccggc ccgagcactc     120
agccatcagg agccgaaccc tgcaacgtgc gggacgcaaa actcatcctt ctcgatcttg     180
ttgaaaacgg tagtagcagg atcattcgtc ggtgcggcat tcatcgctgg catacagca     240
```

-continued

```
ggggctagct gtgatgaagt aaagtctccg caggaggtga acaatgtagg aggcggcgcc    300
ccagtgactg cccccctacac ggtcactttt gcgtccaatt atcatgatcg agtggacaca   360
aaacttcata gagcttatcc tgagttttta cagtaccatc ttattcatga aacgcttcga   420
ggcaaggaaa agatagaggg ctacgagggtg tacaaagata ggcgtgacga ttctatcgta  480
gcatttgctc gcctcgggaa gcttctcagc gggcatccgg atataatcca tggaggctct   540
atagccgcct tactcgacaa cactatgggc gtggcattct tcgctgccaa taaaggtaat   600
ggcttcactg ccaacctcac aatcaattac aagaggccga tcatttgtgg caccgagatc   660
aaggtcttgg cccgagtgga gcggtttgaa ggacgcaagg ttttcctacg agcagagatt   720
cgagatgcta aggacgaggc agtgttgtac acggaagcca catccctctt cataacttca   780
caaagtcctc tgcttacggg accgaagaag gtggacatca gttag                   825
```

<210> SEQ ID NO 3
<211> LENGTH: 37
<212> TYPE: DNA
<213> ORGANISM: Artificial Sequence
<220> FEATURE:
<223> OTHER INFORMATION: PCR primer 1 for NTE

<400> SEQUENCE: 3

```
gcggccgctc tagagccggc ccgagcactc agccatc                             37
```

<210> SEQ ID NO 4
<211> LENGTH: 37
<212> TYPE: DNA
<213> ORGANISM: Artificial Sequence
<220> FEATURE:
<223> OTHER INFORMATION: PCR primer 2 for NTE

<400> SEQUENCE: 4

```
acaaaatatt aacgcctaac tgatgtccac cttcttc                             37
```

<210> SEQ ID NO 5
<211> LENGTH: 20
<212> TYPE: DNA
<213> ORGANISM: Artificial Sequence
<220> FEATURE:
<223> OTHER INFORMATION: PCR primer 1 for vector

<400> SEQUENCE: 5

```
ctctagagcg gccgccaccg                                                20
```

<210> SEQ ID NO 6
<211> LENGTH: 24
<212> TYPE: DNA
<213> ORGANISM: Artificial Sequence
<220> FEATURE:
<223> OTHER INFORMATION: PCR primer 2 for vector

<400> SEQUENCE: 6

```
gcgttaatat tttgttaaaa ttcg                                           24
```

<210> SEQ ID NO 7
<211> LENGTH: 36
<212> TYPE: DNA
<213> ORGANISM: Artificial Sequence
<220> FEATURE:
<223> OTHER INFORMATION: PCR primer 3 for NTE

<400> SEQUENCE: 7

```
gcggccgctc tagagtcatc cttctcgatc ttgttg                              36
```

<210> SEQ ID NO 8
<211> LENGTH: 35
<212> TYPE: DNA
<213> ORGANISM: Artificial Sequence
<220> FEATURE:
<223> OTHER INFORMATION: PCR primer 4 for NTE

<400> SEQUENCE: 8
gcggccgctc tagaggtagc aggatcattc gtcgg                                   35

<210> SEQ ID NO 9
<211> LENGTH: 35
<212> TYPE: DNA
<213> ORGANISM: Artificial Sequence
<220> FEATURE:
<223> OTHER INFORMATION: PCR primer 5 for NTE

<400> SEQUENCE: 9
gcggccgctc tagagatcgc tgggcataca gcagg                                   35

<210> SEQ ID NO 10
<211> LENGTH: 36
<212> TYPE: DNA
<213> ORGANISM: Artificial Sequence
<220> FEATURE:
<223> OTHER INFORMATION: PCR primer 6 for NTE

<400> SEQUENCE: 10
gcggccgctc tagaggatga agtaaagtct ccgcag                                  36

<210> SEQ ID NO 11
<211> LENGTH: 37
<212> TYPE: DNA
<213> ORGANISM: Artificial Sequence
<220> FEATURE:
<223> OTHER INFORMATION: PCR primer 7 for NTE

<400> SEQUENCE: 11
gcggccgctc tagagaatgt aggaggcggc gccccag                                 37

<210> SEQ ID NO 12
<211> LENGTH: 35
<212> TYPE: DNA
<213> ORGANISM: Artificial Sequence
<220> FEATURE:
<223> OTHER INFORMATION: PCR primer 8 for NTE

<400> SEQUENCE: 12
gcggccgctc tagagcccta cacggtcact tttgc                                   35

<210> SEQ ID NO 13
<211> LENGTH: 37
<212> TYPE: DNA
<213> ORGANISM: Artificial Sequence
<220> FEATURE:
<223> OTHER INFORMATION: PCR primer 9 for NTE

<400> SEQUENCE: 13
gcggccgctc tagagcatga tcgagtggac acaaaac                                 37

<210> SEQ ID NO 14
<211> LENGTH: 287
<212> TYPE: PRT
<213> ORGANISM: Nannochloropsis oculata NIES2145

<400> SEQUENCE: 14

| | | | | | | | | | | | | | | |
|---|---|---|---|---|---|---|---|---|---|---|---|---|---|---|
|Met|Thr|Pro|Leu|Ala|Phe|Thr|Val|Leu|Gly|Lys|Leu|Gly|Gly|Thr|Leu|
|1| | |5| | | |10| | | |15| | | |

Thr Phe Ala Cys Val Arg Arg Leu Tyr His Leu Leu Arg Arg Ala
            20                  25                  30

Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Thr Ala Ala Val Val Ala Ala Ile
65                  70                  75                  80

Ser Leu Pro Ser Pro Ser Leu Cys Glu Thr Ala His Ala Gly Thr Glu
            85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
            115                 120                 125

Asp Arg Val Asp Thr Lys Leu His Arg Ala Tyr Pro Glu Phe Leu Lys
130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
            195                 200                 205

Ala Lys Arg Gly Asn Gly Phe Thr Ala Asn Leu Thr Ile Asn Tyr Lys
            210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
        275                 280                 285

<210> SEQ ID NO 15
<211> LENGTH: 864
<212> TYPE: DNA
<213> ORGANISM: Nannochloropsis oculata NIES2145

<400> SEQUENCE: 15

```
atgacgcctt tggccttcac ggtgctcggc aagcttggtg gcacgttgac ttttgcttgt    60
gtacgacgga ggctttatca cttgttacgg cgggcaactt tgtcctccca ttatcaggtc   120
actcggcctt acggtcacag caattccggc tgttcacata gcactaccac acttagaacc   180
agcttcccag tctctctttgc gcaattggca gcagccactg ctgccgtcgt cgctgccatt   240
tccctgccgt cgcctagtct atgcgagacg gcccacgccg ggactgagga gagacgaggt   300
gagaggaagg caatgaggga ggatggtgga aaaggcgagg ccacctcgtc tgctacatgc   360
aatccatcct tattcgaaca tcatgatcgc gtcgacacca agctgcatcg ggcctatcct   420
gaattcctga agttccacct tatccacgag acgctccgag gcaaagagaa aattgatggc   480
```

```
tacgaagttt acaaagacag gcgggatgat tcaattgtgg cgtatgctcg ccttggcaaa    540
ctgctgagcg acaccccga cataatccac ggagggtcca ttgcggcttt gctggacaat    600
accatgggag ttgccttttt cgccgccaag cgtggcaatg gttttacagc aaatctcacc    660
atcaactaca agcgacccat cacgtgtggc accgaagtca agttttagc tcgagtagag    720 aaggtggaag ggcgcaaggt cttcttgcgg gccgagattc gagacgctaa ggatgaggct    780
atcctctaca ctgaagccaa atccctcttc atcacgtctc aaagtccttt attgaaggc    840 ccaaagaaaa ttgatattag ctag                                           864

<210> SEQ ID NO 16
<211> LENGTH: 285
<212> TYPE: PRT
<213> ORGANISM: Nannochloropsis granulata NIES2588

<400> SEQUENCE: 16

Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
            20                  25                  30

Ala Ser Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285

<210> SEQ ID NO 17
```

<211> LENGTH: 858
<212> TYPE: DNA
<213> ORGANISM: Nannochloropsis granulata NIES2588

<400> SEQUENCE: 17

| | |
|---|---|
| atgacgcctt tggccttcac ggcgctcggc gaggtcggtg gcatgttggc tgctgcctgt | 60 |
| gtacgacgga agcttcatca cttgttgcgg cgggcagctt cgtcctccca ggtcactcga | 120 |
| ccttacagtc acagcaccgc caacagcaca catagcacca ccacacttag caacagcttt | 180 |
| ccagtcctct ttgcgcaact cgcagcagcc gctgctgccg tcatggctgc cacttccctg | 240 |
| tcgtcgccca gtctatgtga gacggccac accaatactg aggagagagg aggcgaaggg | 300 |
| gaggcaatga gggagaaggg tggggaaggc gaggccactt cgtctgctac atgcgctcca | 360 |
| tctttcttcg agcatcatga tcgcgtcgac acgaagctgc atcgggccta tcccgagttt | 420 |
| ctgaagttcc acctcatcca cgagacgctc cgagggaaag agaaaattga tggctacgaa | 480 |
| gtatacaaaa acaggcggga cgattcagtt gtggcgtatg ctcgcctggg caaactgctg | 540 |
| agcggacacc ctgacataat tcacggaggg tccatcgctg ctttgctgga caacaccatg | 600 |
| ggagttgcct ttttcgccgc caagcgcggc aatggtttca cagcaaatct caccatcaac | 660 |
| tacaagcgac ccatcacgtg tggcaccgag gtcaaagttc tggctcgagt agagaaggtg | 720 |
| gaggggcgca aggtcttttt gcgggctgag atcagggacg ccaaggatga ggctatcctt | 780 |
| tacactgaag ccaactccct cttcatcacg tcgcaaagcc ctctattgaa gggcccaaag | 840 |
| aaaattgaca ttagctag | 858 |

<210> SEQ ID NO 18
<211> LENGTH: 35
<212> TYPE: DNA
<213> ORGANISM: Artificial Sequence
<220> FEATURE:
<223> OTHER INFORMATION: PCR primer 1 for NoTE

<400> SEQUENCE: 18

| | |
|---|---|
| gcggccgctc tagagatgac gcctttggcc ttcac | 35 |

<210> SEQ ID NO 19
<211> LENGTH: 35
<212> TYPE: DNA
<213> ORGANISM: Artificial Sequence
<220> FEATURE:
<223> OTHER INFORMATION: PCR primer 2 for NoTE

<400> SEQUENCE: 19

| | |
|---|---|
| gcggccgctc tagagtccgg ctgttcacat agcac | 35 |

<210> SEQ ID NO 20
<211> LENGTH: 36
<212> TYPE: DNA
<213> ORGANISM: Artificial Sequence
<220> FEATURE:
<223> OTHER INFORMATION: PCR primer 3 for NoTE

<400> SEQUENCE: 20

| | |
|---|---|
| gcggccgctc tagagcttag aaccagcttc ccagtc | 36 |

<210> SEQ ID NO 21
<211> LENGTH: 36
<212> TYPE: DNA
<213> ORGANISM: Artificial Sequence
<220> FEATURE:
<223> OTHER INFORMATION: PCR primer 4 for NoTE

```
<400> SEQUENCE: 21
gcggccgctc tagaggctgc catttccctg ccgtcg                                    36

<210> SEQ ID NO 22
<211> LENGTH: 38
<212> TYPE: DNA
<213> ORGANISM: Artificial Sequence
<220> FEATURE:
<223> OTHER INFORMATION: PCR primer 5 for NoTE

<400> SEQUENCE: 22
gcggccgctc tagagtgcga cacggcccac gccgggac                                  38

<210> SEQ ID NO 23
<211> LENGTH: 35
<212> TYPE: DNA
<213> ORGANISM: Artificial Sequence
<220> FEATURE:
<223> OTHER INFORMATION: PCR primer 6 for NoTE

<400> SEQUENCE: 23
gcggccgctc tagagagacg aggtgagagg aaggc                                     35

<210> SEQ ID NO 24
<211> LENGTH: 36
<212> TYPE: DNA
<213> ORGANISM: Artificial Sequence
<220> FEATURE:
<223> OTHER INFORMATION: PCR primer 7 for NoTE

<400> SEQUENCE: 24
gcggccgctc tagaggatgg tggaaaaggc gaggcc                                    36

<210> SEQ ID NO 25
<211> LENGTH: 39
<212> TYPE: DNA
<213> ORGANISM: Artificial Sequence
<220> FEATURE:
<223> OTHER INFORMATION: PCR primer 8 for NoTE

<400> SEQUENCE: 25
gcggccgctc tagaggctac atgcaatcca tccttattc                                 39

<210> SEQ ID NO 26
<211> LENGTH: 37
<212> TYPE: DNA
<213> ORGANISM: Artificial Sequence
<220> FEATURE:
<223> OTHER INFORMATION: PCR primer 9 for NoTE

<400> SEQUENCE: 26
gcggccgctc tagagcatga tcgcgtcgac accaagc                                   37

<210> SEQ ID NO 27
<211> LENGTH: 39
<212> TYPE: DNA
<213> ORGANISM: Artificial Sequence
<220> FEATURE:
<223> OTHER INFORMATION: PCR primer 10 for NoTE

<400> SEQUENCE: 27
acaaaatatt aacgcctagc taatatcaat tttctttgg                                 39

<210> SEQ ID NO 28
```

```
<211> LENGTH: 35
<212> TYPE: DNA
<213> ORGANISM: Artificial Sequence
<220> FEATURE:
<223> OTHER INFORMATION: PCR primer 1 for NgrTE

<400> SEQUENCE: 28
gcggccgctc tagagatgac gcctttggcc ttcac                          35

<210> SEQ ID NO 29
<211> LENGTH: 35
<212> TYPE: DNA
<213> ORGANISM: Artificial Sequence
<220> FEATURE:
<223> OTHER INFORMATION: PCR primer 2 for NgrTE

<400> SEQUENCE: 29
gcggccgctc tagagtcctc ccaggtcact cgacc                          35

<210> SEQ ID NO 30
<211> LENGTH: 35
<212> TYPE: DNA
<213> ORGANISM: Artificial Sequence
<220> FEATURE:
<223> OTHER INFORMATION: PCR primer 3 for NgrTE

<400> SEQUENCE: 30
gcggccgctc tagagacact tagcaacagc tttcc                          35

<210> SEQ ID NO 31
<211> LENGTH: 35
<212> TYPE: DNA
<213> ORGANISM: Artificial Sequence
<220> FEATURE:
<223> OTHER INFORMATION: PCR primer 4 for NgrTE

<400> SEQUENCE: 31
gcggccgctc tagagctatg tgagacggcc cacac                          35

<210> SEQ ID NO 32
<211> LENGTH: 36
<212> TYPE: DNA
<213> ORGANISM: Artificial Sequence
<220> FEATURE:
<223> OTHER INFORMATION: PCR primer 5 for NgrTE

<400> SEQUENCE: 32
gcggccgctc tagagcatga tcgcgtcgac acgaag                         36

<210> SEQ ID NO 33
<211> LENGTH: 39
<212> TYPE: DNA
<213> ORGANISM: Artificial Sequence
<220> FEATURE:
<223> OTHER INFORMATION: PCR primer 6 for NgrTE

<400> SEQUENCE: 33
acaaaatatt aacgcctagc taatgtcaat tttctttgg                      39

<210> SEQ ID NO 34
<211> LENGTH: 287
<212> TYPE: PRT
<213> ORGANISM: Artificial Sequence
<220> FEATURE:
<223> OTHER INFORMATION: NoTE mutant

<400> SEQUENCE: 34
```

```
Met Thr Pro Leu Ala Phe Thr Val Leu Gly Lys Leu Gly Gly Thr Leu
1               5                   10                  15

Thr Phe Ala Cys Val Arg Arg Leu Tyr His Leu Leu Arg Arg Ala
            20              25              30

Thr Leu Ser Ser His Tyr Gln Val Thr Arg Pro Tyr Gly His Ser Asn
        35                  40                  45

Ser Gly Cys Ser His Ser Thr Thr Leu Arg Thr Ser Phe Pro Val
    50              55                  60

Leu Phe Ala Gln Leu Ala Ala Thr Ala Ala Val Val Ala Ala Ile
65              70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
            115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
            195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Cys Val Glu
225                 230                 235                 240

Lys Val Glu Arg Gln Lys Lys Val Phe Leu Arg Ala Val Ile Arg Asp
                245                 250                 255

Ala Lys Asp Glu Ala Ile Leu Tyr Ala Glu Ala Lys Ser Leu Phe Ile
            260                 265                 270

Ser Ser Gln Ser Pro Leu Lys Ala Pro Arg Lys Ile Ala Thr Ser
            275                 280                 285
```

<210> SEQ ID NO 35
<211> LENGTH: 864
<212> TYPE: DNA
<213> ORGANISM: Artificial Sequence
<220> FEATURE:
<223> OTHER INFORMATION: NoTE mutant

<400> SEQUENCE: 35

```
atgacgcctt tggccttcac ggtgctcggc aagcttggtg gcacgttgac ttttgcttgt   60
gtacgacgga ggctttatca cttgttacgg cgggcaactt tgtcctccca ttatcaggtc  120
actcggcctt acggtcacag caattccggc tgttcacata gcactaccac acttagaacc  180
agcttcccag tcctctttgc gcaattggca gcagccactg ctgccgtcgt cgctgccatt  240
tccctgccgt cgcctagtct atgcgagacg gcccacgccg gactgaggag agacgaggt  300 gagaggaagg caatgaggga ggatggtgga aaaggcgagg ccacctcgtc tgctacatgc  360
aatccatcct tattcgaaca tcatgatcgc gtcgacacca agctgcatcg ggcctatcct  420
```

```
gaattcctga agttccacct tatccacgag acgctccgag gcaaagagaa aattgatggc    480
tacgaagttt acaaagacag gcgggatgat tcaattgtgg cgtatgctcg ccttggcaaa    540
ctgctgagcg gacaccccga cataatccac ggagggtcca ttgcggcttt gctggacaat    600
accatgggag ttgccttttt cgccgccaag cgtggcaatg ttttacagc aaatctcacc     660 atcaactaca agcgacccat cacgtgtggc accgaagtca agttttagc ttgtgtagag     720 aaggtggaac gccagaaaaa ggtcttcttg cgggccgtga ttcgagacgc taaggatgag    780
gctatcctct acgctgaagc caaatccctc ttcatctcgt ctcaaagtcc tttaaaggcc    840
ccacggaaaa ttgctactag ctag                                           864
```

```
<210> SEQ ID NO 36
<211> LENGTH: 35
<212> TYPE: DNA
<213> ORGANISM: Artificial Sequence
<220> FEATURE:
<223> OTHER INFORMATION: PCR primer for NoTE mutant

<400> SEQUENCE: 36
acaaaatatt aacgcctagc tagtagcaat tttcc                               35

<210> SEQ ID NO 37
<211> LENGTH: 35
<212> TYPE: DNA
<213> ORGANISM: Artificial Sequence
<220> FEATURE:
<223> OTHER INFORMATION: PCR primer 1 for NoTE 292

<400> SEQUENCE: 37
cgcggtgttg cgcgcagacg aggtgagagg aaggc                               35

<210> SEQ ID NO 38
<211> LENGTH: 39
<212> TYPE: DNA
<213> ORGANISM: Artificial Sequence
<220> FEATURE:
<223> OTHER INFORMATION: PCR primer 2 for NoTE 292

<400> SEQUENCE: 38
ctcttccaca gaagcctagc taatatcaat tttctttgg                            39

<210> SEQ ID NO 39
<211> LENGTH: 37
<212> TYPE: DNA
<213> ORGANISM: Artificial Sequence
<220> FEATURE:
<223> OTHER INFORMATION: PCR primer 1 for VCP1 promoter

<400> SEQUENCE: 39
cgagctcggt acccgggcgg tcttttgtcc tttcctc                              37

<210> SEQ ID NO 40
<211> LENGTH: 22
<212> TYPE: DNA
<213> ORGANISM: Artificial Sequence
<220> FEATURE:
<223> OTHER INFORMATION: PCR primer 2 for VCP1 promoter

<400> SEQUENCE: 40
aatctgctcg gagggagga tc                                               22

<210> SEQ ID NO 41
<211> LENGTH: 36
```

<212> TYPE: DNA
<213> ORGANISM: Artificial Sequence
<220> FEATURE:
<223> OTHER INFORMATION: PCR primer 1 for VCP1 chloroplast transit
      signal

<400> SEQUENCE: 41
ccctccgagc agattatgaa gaccgccgct ctcctc                                     36

<210> SEQ ID NO 42
<211> LENGTH: 28
<212> TYPE: DNA
<213> ORGANISM: Artificial Sequence
<220> FEATURE:
<223> OTHER INFORMATION: PCR primer 2 for VCP1 chloroplast transit
      signal

<400> SEQUENCE: 42
gcgcgcaaca ccgcgggtgc gggagaac                                              28

<210> SEQ ID NO 43
<211> LENGTH: 21
<212> TYPE: DNA
<213> ORGANISM: Artificial Sequence
<220> FEATURE:
<223> OTHER INFORMATION: PCR primer 1 for VCP1 terminator

<400> SEQUENCE: 43
gcttctgtgg aagagccagt g                                                     21

<210> SEQ ID NO 44
<211> LENGTH: 35
<212> TYPE: DNA
<213> ORGANISM: Artificial Sequence
<220> FEATURE:
<223> OTHER INFORMATION: PCR primer 2 for VCP1 terminator

<400> SEQUENCE: 44
actctagagg atcccctgat cttgtccatc tcgtg                                      35

<210> SEQ ID NO 45
<211> LENGTH: 20
<212> TYPE: DNA
<213> ORGANISM: Artificial Sequence
<220> FEATURE:
<223> OTHER INFORMATION: PCR primer 1 for plasmid pUC19

<400> SEQUENCE: 45
gggatcctct agagtcgacc                                                       20

<210> SEQ ID NO 46
<211> LENGTH: 20
<212> TYPE: DNA
<213> ORGANISM: Artificial Sequence
<220> FEATURE:
<223> OTHER INFORMATION: PCR primer 2 for plasmid pUC19

<400> SEQUENCE: 46
cgggtaccga gctcgaattc                                                       20

<210> SEQ ID NO 47
<211> LENGTH: 37
<212> TYPE: DNA
<213> ORGANISM: Artificial Sequence
<220> FEATURE:
<223> OTHER INFORMATION: PCR primer 1 for zeocin resistance gene

<400> SEQUENCE: 47
cttttttgtg aagcaatggc caagttgacc agtgccg 37

<210> SEQ ID NO 48
<211> LENGTH: 37
<212> TYPE: DNA
<213> ORGANISM: Artificial Sequence
<220> FEATURE:
<223> OTHER INFORMATION: PCR primer 2 for zeocin resistance gene

<400> SEQUENCE: 48
ctcttccaca gaagcttagt cctgctcctc ggccacg 37

<210> SEQ ID NO 49
<211> LENGTH: 35
<212> TYPE: DNA
<213> ORGANISM: Artificial Sequence
<220> FEATURE:
<223> OTHER INFORMATION: PCR primer 1 for tubulin promoter

<400> SEQUENCE: 49
cgagctcggt acccgactgc gcatggattg accga 35

<210> SEQ ID NO 50
<211> LENGTH: 28
<212> TYPE: DNA
<213> ORGANISM: Artificial Sequence
<220> FEATURE:
<223> OTHER INFORMATION: PCR primer 2 for tubulin promoter

<400> SEQUENCE: 50
tgcttcacaa aaagacagc ttcttgat 28

<210> SEQ ID NO 51
<211> LENGTH: 22
<212> TYPE: DNA
<213> ORGANISM: Artificial Sequence
<220> FEATURE:
<223> OTHER INFORMATION: PCR primer 1 for DNA fragment containing NoTE

<400> SEQUENCE: 51
ggcggtcttt tgtcctttcc tc 22

<210> SEQ ID NO 52
<211> LENGTH: 20
<212> TYPE: DNA
<213> ORGANISM: Artificial Sequence
<220> FEATURE:
<223> OTHER INFORMATION: PCR primer 2 for DNA fragment containing NoTE

<400> SEQUENCE: 52
ctgatcttgt ccatctcgtg 20

<210> SEQ ID NO 53
<211> LENGTH: 20
<212> TYPE: DNA
<213> ORGANISM: Artificial Sequence
<220> FEATURE:
<223> OTHER INFORMATION: PCR primer 1 for DNA fragment containing zeocin
      resistance gene

<400> SEQUENCE: 53
actgcgcatg gattgaccga 20

<210> SEQ ID NO 54

<211> LENGTH: 802
<212> TYPE: DNA
<213> ORGANISM: Artificial Sequence
<220> FEATURE:
<223> OTHER INFORMATION: VCP1 promoter

<400> SEQUENCE: 54

| | |
|---|---|
| ggcggtcttt tgtcctttcc tctatagccc gcccgtctag agggcacacg cgatgatctt | 60 |
| tatatctctt catgtgtctt tgttttaact aggatactgc cgggtgaatg cccatcggac | 120 |
| aagaggccaa actctatcta caccctttg acttctgttg tggtcgtagt gtgtgcttgc | 180 |
| atgccctgaa agtccaggca tcccacttgt gctctaaccc cattcaaaac agcagaagtg | 240 |
| cttaattaag atatagattc atgatctcct gtccctcct tcttacctt tcacaaacct | 300 |
| cacacagaag tctccactct tcgcctctaa aacctctttt taaattatgg taagttcgtg | 360 |
| cggcagtggg ttttcggatc tatatttgtc aagatccagt tcaaggtcag ggatgtagat | 420 |
| taagtacaga aggagaagca caagcgcgcc agttcgcccc tcacggcctg gagcagggca | 480 |
| tttaatccct ctatcttacc agaaccatac tatacaacca atcctgttgg catcgctctg | 540 |
| tctatttgtc gtgcgtgcat gtgtccatgg tgtggtgggg gcagggttt ttcggggttg | 600 |
| cggttgaagg caccttatca gaaagatgcc ctcagagata gaggtagccc cctcccccg | 660 |
| atcttcgacc agtcctgtca ggcgaacact ttcacccgtc gttcacctcg ttacacacaa | 720 |
| ggagtagacc tctgaagttc taattgtcat aaatgcccct ccccctccc tctttccctt | 780 |
| gatcctcccc tccgagcaga tt | 802 |

<210> SEQ ID NO 55
<211> LENGTH: 99
<212> TYPE: DNA
<213> ORGANISM: Artificial Sequence
<220> FEATURE:
<223> OTHER INFORMATION: VCP1 chloroplast transit signal

<400> SEQUENCE: 55

| | |
|---|---|
| atgaagaccg ccgctctcct cactgtctcc accctcatgg gcgcccaggc ctttatggcc | 60 |
| cccgcccca gttctcccg cacccgcggt gttgcgcgc | 99 |

<210> SEQ ID NO 56
<211> LENGTH: 643
<212> TYPE: DNA
<213> ORGANISM: Artificial Sequence
<220> FEATURE:
<223> OTHER INFORMATION: VCP1 terminator

<400> SEQUENCE: 56

| | |
|---|---|
| gcttctgtgg aagagccagt ggtagtagca gtagcagcag cagtagcagc cgcagcactc | 60 |
| agtgttggcg cgagagattg tccatccctt cttaacctac cggaagagaa ataaggcctt | 120 |
| tctcccgtag ctgtcttcgt ttgttttgtgc tgattgcttg atatgagagt gttgaattcc | 180 |
| tgcatcatgt ttttctctgt agtcctttcc tacccccgtc attttctttt ctccctggtt | 240 |
| cttcttttgt caccttatt ttacataaaa ttttctttgt ttatagtgag aggaaggtag | 300 |
| agagggaaa acaagaacaa cgaacgcaag cgtgtgaaag gagggcgagt agaagagaaa | 360 |
| cagatctgtt gagcattgag agtggagccg ggggaaaggc ttgtgtgttg tctttgaaaa | 420 |
| agttgtttaa atcacgaatc cgttagttct catgtgtacc tctttcacta catgtgatgg | 480 |
| agaaaacaaa agtgtgagga ttaattgaag aaaaagaaga gttcgacacg tcaaaccgcc | 540 |
| caaaagacgt cacaaagaga acttgattct ctttgccgtg ttgatcctgt cttttccccc | 600 | agcttttctt gccacccgtg gcacacgaga tggacaagat cag        643

<210> SEQ ID NO 57
<211> LENGTH: 2117
<212> TYPE: DNA
<213> ORGANISM: Artificial Sequence
<220> FEATURE:
<223> OTHER INFORMATION: DNA fragment containing NoTE

<400> SEQUENCE: 57

```
ggcggtcttt tgtcctttcc tctatagccc gcccgtctag agggcacacg cgatgatctt     60
tatatctctt catgtgtctt tgttttaact aggatactgc cgggtgaatg cccatcggac    120
aagaggccaa actctatcta cacccttttg acttctgttg tggtcgtagt gtgtgcttgc    180
atgccctgaa agtccaggca tcccacttgt gctctaaccc cattcaaaac agcagaagtg    240
cttaattaag atatagattc atgatctcct gtccctcct tcttaccttt tcacaaacct    300
cacacagaag tctccactct tcgcctctaa aacctctttt taaattatgg taagttcgtg    360
cggcagtggg ttttcggatc tatatttgtc aagatccagt tcaaggtcag ggatgtagat    420
taagtacaga aggagaagca caagcgcgcc agttcgcccc tcacggcctg gagcagggca    480
tttaatccct ctatcttacc agaaccatac tatacaacca atcctgttgg catcgctctg    540
tctatttgtc gtgcgtgcat gtgtccatgg tgtggtgggg ggcaggggtt ttcgggttg    600
cggttgaagg caccttatca gaaagatgcc ctcagagata gaggtagccc cctcccccg    660
atcttcgacc agtcctgtca ggcgaacact ttcacccgtc gttcacctcg ttacacacaa    720
ggagtagacc tctgaagttc taattgtcat aaatgcccct ccccctcc tctttcctt      780
gatcctcccc tccgagcaga ttatgaagac cgccgctctc ctcactgtct ccaccctcat    840
gggcgcccag gcctttatgg cccccgcccc caagttctcc cgcacccgcg tgttgcgcg    900
cagacgaggt gagaggaagg caatgaggga ggatggtgga aaaggcgagg ccacctcgtc    960
tgctacatgc aatccatcct tattcgaaca tcatgatcgc gtcgacacca agctgcatcg   1020
ggcctatcct gaattcctga agttccacct tatccacgag acgctccgag gcaaagagaa   1080
aattgatggc tacgaagttt acaaagacag gcgggatgat tcaattgtgg cgtatgctcg   1140
ccttggcaaa ctgctgagcg acaccccga cataatccac ggagggtcca ttgcggcttt   1200
gctgacaat accatgggag ttgccttttt cgccgccaag cgtggcaatg gttttacagc   1260
aaatctcacc atcaactaca gcgacccat cacgtgtggc accgaagtca agttttagc   1320
tcgagtagag aaggtggaag ggcgcaaggt cttcttgcgg gccagagattc gagacgctaa   1380
ggatgaggct atcctctaca ctgaagccaa atccctcttc atcacgtctc aaagtccttt   1440
attgaagggc ccaaagaaaa ttgatattag ctaggcttct gtggaagagc cagtggtagt   1500
agcagtagca gcagcagtag cagccgcagc actcagtgtt ggcgcgagag attgtccatc   1560
ccttcttaac ctaccggaag agaaataagg cctttctccc gtagctgtct tcgtttgttt   1620
gtgctgattg cttgatatga gagtgttgaa ttcctgcatc atgttttttct ctgtagtcct   1680
ttcctacccc cgtcatttc ttttctcct ggttcttctt ttgtcaccct tatttttacat   1740
aaaatttttct ttgtttatag tgagaggaag gtagagaggg gaaaacaaga acaacgaacg   1800
caagcgtgtg aaaggagggc gagtagaaga gaaacagatc tgttgagcat tgagagtgga   1860
gccggggaa aggcttgtgt gttgtctttg aaaaagttgt ttaaatcacg aatccgttag   1920
ttctcatgtg tacctctttc actacatgtg atggagaaaa caaagtgtg aggattaatt   1980
```

| gaagaaaaag aagagttcga cacgtcaaac cgcccaaaag acgtcacaaa gagaacttga | 2040 |
| ttctctttgc cgtgttgatc ctgtcttttc ccccagcttt tcttgccacc cgtggcacac | 2100 |
| gagatggaca agatcag | 2117 |

```
<210> SEQ ID NO 58
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 58
```

| atggccaagt tgaccagtgc cgttccggtg ctcaccgcgc gcgacgtcgc cggagcggtc | 60 |
| gagttctgga ccgaccggct cgggttctcc cgggacttcg tggaggacga cttcgccggt | 120 |
| gtggtccggg acgacgtgac cctgttcatc agcgcggtcc aggaccaggt ggtgccggac | 180 |
| aacaccctgg cctgggtgtg ggtgcgcggc ctggacgagc tgtacgccga gtggtcggag | 240 |
| gtcgtgtcca cgaacttccg ggacgcctcc gggccggcca tgaccgagat cggcgagcag | 300 |
| ccgtgggggc gggagttcgc cctgcgcgac ccggccggca actgcgtgca cttcgtggcc | 360 |
| gaggagcagg actaa | 375 |

```
<210> SEQ ID NO 59
<211> LENGTH: 500
<212> TYPE: DNA
<213> ORGANISM: Artificial Sequence
<220> FEATURE:
<223> OTHER INFORMATION: Tubulin promoter

<400> SEQUENCE: 59
```

| actgcgcatg gattgaccga cggccggttg ccaacttttg gggtcggccc cccttttcta | 60 |
| gcccttgccc gtccagcaat taaaaattat caacggcata ccggcactgg aagcttcggg | 120 |
| tttacaattt tggcttgcct tcctaatact gtaccgcgga gaacgtatga tattacagaa | 180 |
| aaatgccttg cacagttagc gcaaagggaa aacgtttctc cgccattgta cttttttggaa | 240 |
| gagggaaagc gattgtaaaa tatggctctc cgctacgaga gtttgggctg ttgatacatg | 300 |
| tgaaaataag tgtggacgac tttgaatgac ttgatcaggc tgtttgcaca tataaccagc | 360 |
| gcgcatgcac ttctgacatg tcaatgacga aatttcacac ttcaccaata aattgtatcc | 420 |
| ttacgttttg tctttctcac acgcacatat atgatcatag ataaaagcca atatcaagaa | 480 |
| gctgtctttt ttgtgaagca | 500 |

```
<210> SEQ ID NO 60
<211> LENGTH: 1518
<212> TYPE: DNA
<213> ORGANISM: Artificial Sequence
<220> FEATURE:
<223> OTHER INFORMATION: DNA fragment containing zeocin resistance gene

<400> SEQUENCE: 60
```

| actgcgcatg gattgaccga cggccggttg ccaacttttg gggtcggccc cccttttcta | 60 |
| gcccttgccc gtccagcaat taaaaattat caacggcata ccggcactgg aagcttcggg | 120 |
| tttacaattt tggcttgcct tcctaatact gtaccgcgga gaacgtatga tattacagaa | 180 |
| aaatgccttg cacagttagc gcaaagggaa aacgtttctc cgccattgta cttttttggaa | 240 |
| gagggaaagc gattgtaaaa tatggctctc cgctacgaga gtttgggctg ttgatacatg | 300 |
| tgaaaataag tgtggacgac tttgaatgac ttgatcaggc tgtttgcaca tataaccagc | 360 |

```
gcgcatgcac ttctgacatg tcaatgacga aatttcacac ttcaccaata aattgtatcc    420
ttacgttttg tctttctcac acgcacatat atgatcatag ataaaagcca atatcaagaa    480
gctgtctttt ttgtgaagca atggccaagt tgaccagtgc cgttccggtg ctcaccgcgc    540
gcgacgtcgc cggagcggtc gagttctgga ccgaccggct cgggttctcc cgggacttcg    600
tggaggacga cttcgccggt gtggtccggg acgacgtgac cctgttcatc agcgcggtcc    660
aggaccaggt ggtgccggac aacaccctgg cctgggtgtg ggtgcgcggc ctggacgagc    720
tgtacgccga gtggtcggag gtcgtgtcca cgaacttccg ggacgcctcc gggccggcca    780
tgaccgagat cggcgagcag ccgtgggggc gggagttcgc cctgcgcgac ccggccggca    840
actgcgtgca cttcgtggcc gaggagcagg actaagcttc tgtggaagag ccagtggtag    900
tagcagtagc agcagcagta gcagccgcag cactcagtgt tggcgcgaga gattgtccat    960
cccttcttaa cctaccggaa gagaaataag gcctttctcc cgtagctgtc ttcgtttgtt   1020
tgtgctgatt gcttgatatg agagtgttga attcctgcat catgttttc tctgtagtcc    1080 tttcctaccc ccgtcatttt cttttctccc tggttcttct tttgtcaccc ttatttaca    1140 taaaattttc tttgtttata gtgagaggaa ggtagagagg ggaaaacaag aacaacgaac   1200
gcaagcgtgt gaaaggaggg cgagtagaag agaaacagat ctgttgagca ttgagagtgg   1260
agccggggga aaggcttgtg tgttgtcttt gaaaaagttg tttaaatcac gaatccgtta   1320
gttctcatgt gtacctcttt cactacatgt gatggagaaa acaaaagtgt gaggattaat   1380
tgaagaaaaa gaagagttcg acacgtcaaa ccgcccaaaa gacgtcacaa agagaacttg   1440
attctctttg ccgtgttgat cctgtctttt cccccagctt ttcttgccac ccgtggcaca   1500
cgagatggac aagatcag                                                 1518
```

ACYL-ACP THIOESTERASE

TECHNICAL FIELD

The present invention relates to a novel acyl-ACP thioesterase, and a gene encoding the same. Further, the present invention relates to a transformant having the acyl-ACP thioesterase gene and a method of producing a lipid using the same.

BACKGROUND ART

Fatty acids are one of the principal components of lipids. In vivo, fatty acids are attached to glycerin via an ester bond to form lipids such as triacylglycerol. Many animals and plants store and utilize fatty acids as an energy source. These fatty acids and lipids are widely utilized for food or industrial use.

For example, higher alcohol derivatives that are obtained by reducing higher fatty acids having approximately 12 to 18 carbon atoms are used as surfactants. Alkyl sulfuric acid ester salts and alkylbenzenesulfonic acid salts are utilized as anionic surfactants, and polyoxyalkylene alkyl ethers and alkyl polyglycosides are utilized as nonionic surfactants. These surfactants are used for detergents or disinfectants. As other higher alcohol derivatives, cationic surfactants such as alkylamine salts and mono- or dialkyl-quaternary amine salts are commonly used for fiber treatment agents, hair conditioning agents or disinfectants, and benzalkonium type quaternary ammonium salts are commonly used for disinfectants or antiseptics. Moreover, vegetable fats and oils are used also as raw materials of biodiesel fuels.

Fatty acids and lipids are widely used for various applications shown above. Therefore, it has been attempted to enhance the productivity of fatty acids or lipids in vivo by using plants and the like. Further, the applications and usefulness of fatty acids depend on the number of carbon atoms. Therefore, controlling of the number of carbon atoms of the fatty acids, namely, a chain length thereof has also been attempted. For example, a method of accumulating fatty acids having 12 carbon atoms by introducing an acyl-ACP thioesterase derived from *Umbellularia californica* (California bay) (Patent Literature 1, and Non-Patent Literature 1) has been proposed.

Attention has been recently focused on algae to the effect that the algae are useful in biofuel production. The algae can produce lipids that can be used as the biodiesel fuels through photosynthesis, and do not compete with foods. Therefore, the algae attract attention as next-generation biomass resources. Moreover, the algae are also reported to the effect that the algae have higher lipid production and accumulation ability in comparison with plants.

Research has started on a lipid synthesis mechanism of the algae and production technologies applying the mechanism, but unclear parts remain in many respects. For example, almost no report has been made so far on the above-mentioned acyl-ACP thioesterase derived from algae, either, and only limited examples of reports are made on Class Diatomea or the like (for example, Non-Patent Literature 2).

CITATION LIST

Patent Literature

Patent Literature 1: JP-A-7-501924 ("JP-A" means unexamined published Japanese patent application)

Non-Patent Literatures

Non-Patent Literature 1: Voelker T A, Worrell A C, Anderson L, Bleibaum J, Fan C, Hawkins D J, Radke S E, Davies H M., "Fatty acid biosynthesis redirected to medium chains in transgenic oilseed plants", Science. 1992 Jul. 3; 257 (5066), p. 72-74.

Non-Patent Literature 2: Yangmin Gong, Xiaojing Guo, Xia Wan, Zhuo Liang, Mulan Jiang, "Characterization of a novel thioesterase (PtTE) from *Phaeodactylum tricornutum*", Journal of Basic Microbiology, 2011 December, Volume 51, p. 666-672.

SUMMARY OF INVENTION

The present invention is contemplated for providing a novel acyl-ACP thioesterase derived from algae, and an acyl-ACP thioesterase gene encoding the same. Further, the present invention is contemplated for providing a transformant having the gene. Furthermore, the present invention is contemplated for providing a method of producing a lipid using the transformant.

The present inventors made extensive studies so as to search a novel acyl-ACP thioesterase derived from algae. As a result, they found that a novel acyl-ACP thioesterase derived from algae belonging to the genus *Nannochloropsis* and an acyl-ACP thioesterase gene encoding the thioesterase. The present invention was completed based on these findings.

The present invention relates to a protein selected from the following (a) to (c):

(a) A protein consisting of an amino acid sequence of the $115^{th}$ to $274^{th}$ amino acids set forth in SEQ ID NO: 1;

(b) A protein consisting of an amino acid sequence having 50% or more identity with the amino acid sequence of the protein (a), and having acyl-ACP thioesterase activity; and (c) A protein containing the amino acid sequence of the protein (a) or (b), and having acyl-ACP thioesterase activity.

(Hereinafter, referred to as "the protein of the present invention" or "the acyl-ACP thioesterase of the present invention")

The present invention also relates to a gene encoding the protein of the present invention, preferably a gene consisting of any one of the following DNAs (d) to (f):

(d) A DNA consisting of a nucleotide sequence of the $343^{rd}$ to $825^{th}$ nucleotides set forth in SEQ ID NO: 2;

(e) A DNA consisting of a nucleotide sequence having 50% or more identity with the nucleotide sequence of the DNA (d), and encoding a protein having acyl-ACP thioesterase activity; and (f) A DNA containing the nucleotide sequence of the DNA (d) or the DNA (e), and encoding a protein having acyl-ACP thioesterase activity.

(Hereinafter, referred to as "the gene of the present invention" or "the acyl-ACP thioesterase gene of the present invention")

The present invention also relates to a transformant obtained by introducing the gene of the present invention into a host.

(Hereinafter, referred to as "the transformant of the present invention")

The present invention also relates to a method of producing a lipid, containing steps of:

culturing the transformant of the present invention in a medium; and collecting a lipid from the resulting cultured product. (Hereinafter, referred to as "the method of producing a lipid of the present invention")

The present invention also relates to a method of modifying a fatty acid composition in a lipid, containing introducing the gene of the present invention into a host.

The present invention also relates to a method of enhancing productivity of a lipid, containing introducing the gene of the present invention into a host.

The present invention provides a novel acyl-ACP thioesterase and an acyl-ACP thioesterase gene encoding the same. The present invention also provides a transformant having the acyl-ACP thioesterase gene. Further, the present invention provides a method of producing a lipid using the transformant. The transformant and the production method of the present invention have the excellent productivity of lipids, and therefore they can be suitably used for the industrial production of fatty acids or lipids.

Other and further features and advantages of the invention will appear more fully from the following description.

MODE FOR CARRYING OUT THE INVENTION

Hereinafter, the present invention will be explained.

In the present invention, the term "lipid(s)" covers simple lipids such as neutral lipids, wax, and ceramides; complex lipids such as phospholipids, glycolipids, and sulfolipids; and derived lipids such as fatty acids, alcohols, and hydrocarbons.

1. Acyl-ACP Thioesterase

The protein of the present invention includes a protein at least having an amino acid sequence of the $115^{th}$ to $274^{th}$ amino acids set forth in SEQ ID NO: 1, and a protein functionally equivalent to the protein. Specifically, the protein of the present invention includes the following proteins (a) to (c).

(a) A protein consisting of an amino acid sequence of the $115^{th}$ to $274^{th}$ amino acids set forth in SEQ ID NO: 1.

(b) A protein consisting of an amino acid sequence having 50% or more identity with the amino acid sequence of the protein (a), and having acyl-ACP thioesterase activity.

(c) A protein containing the amino acid sequence of the protein (a) or the protein (b), and having acyl-ACP thioesterase activity.

The protein consisting of the amino acid sequence set forth in SEQ ID NO: 1 is a novel acyl-ACP thioesterase derived from an alga belonging to the genus *Nannochloropsis, Nannochloropsis gaditana*.

The acyl-ACP (acyl carrier protein) thioesterase is an enzyme involved in the biosynthesis pathway of fatty acids and derivatives thereof (such as triacylglycerol (triglyceride)). This enzyme hydrolyzes a thioester bond of an acyl-ACP to form free fatty acids in a plastid such as a chloroplast of plants and algae or in a cytoplasm of bacteria, fungi and animals. The acyl-ACP is a composite composed of an acyl group as a fatty acid residue and an acyl carrier protein, and is an intermediate in the process of fatty acid biosynthesis. The function of the thioesterase completes the synthesis of the fatty acid synthesis on the ACP, and then the thus-produced free fatty acids are supplied to the synthesis of triglyceride and the like. To date, several acyl-ACP thioesterases having different reaction specificities depending on the number of carbon atoms and the number of unsaturated bonds of acylgroup (fatty acid residue) of acyl-ACP substrate are identified. Therefore, they are considered to be an important factor in determining fatty acid composition of an organism.

In the present invention, the "having thioesterase activity" means having an activity of hydrolyzing a thioester bond of an acyl-ACP.

One example of nucleotide sequences encoding the amino acid sequence set forth in SEQ ID NO: 1 is a nucleotide sequence set forth in SEQ ID NO: 2. The gene consisting of the nucleotide sequence set forth in SEQ ID NO: 2 is derived from *Nannochloropsis paditana*. Genome sequence data of *Nannochloropsis gaditana* has been published in 2012 (see Randor Radakovits, et al., "Draft genome sequence and genetic transformation of the oleaginous alga *Nannochloropsis gaditana*", Nature Communications, DO1:10.1038/ncomms1688, 2012).

The present inventors have identified the gene consisting of the nucleotide sequence set forth in SEQ ID NO: 2 as an acyl-ACP thioesterase gene. Further, they have identified an important region for acyl-ACP thioesterase activity in the amino acid sequence encoded by the gene.

A recombinant protein at least having an amino acid sequence of the $115^{th}$ to $274^{th}$ amino acids set forth in SEQ ID NO: 1 acts as an acyl-ACP thioesterase as demonstrated in the working examples below. That is, it is thought that the region from $115^{th}$ to $274^{th}$ amino acids is sufficient for acyl-ACP thioesterase activity, with respect to the amino acid sequence set forth in SEQ ID NO: 1.

In the protein (b), the sequence identity of amino acid sequence is preferably 60% or more, more preferably 70% or more, further preferably 80% or more, further more preferably 90% or more, and particularly preferably 95% or more, in view of acyl-ACP thioesterase activity.

In the present specification, the sequence identity of the amino acid sequence and nucleotide sequence is calculated through the Lipman-Pearson method (see Science, 227, pp. 1435, (1985)). Specifically, the identity can be determined through use of a homology analysis (homology search) program of genetic information processing software Genetyx-Win (Software Development Co., Ltd.) with the unit size to compare (ktup) being set to 2.

Specific examples of the protein (b) include the following proteins (a1) and (a2).

(a1) A protein consisting of an amino acid sequence of the $128^{th}$ to $287^{th}$ amino acids set forth in SEQ ID NO: 14.

(a2) A protein consisting of an amino acid sequence of the $126^{th}$ to $285^{th}$ amino acids set forth in SEQ ID NO: 16.

The protein consisting of the amino acid sequence set forth in SEQ ID NO: 14 is a novel acyl-ACP thioesterase derived from *Nannochloropsis oculata*. The amino acid sequence of the $128^{th}$ to $287^{th}$ amino acids set forth in SEQ ID NO: 14 has about 91% identity with the amino acid sequence of the $115^{th}$ to $274^{th}$ amino acids set forth in SEQ ID NO: 1.

The protein consisting of the amino acid sequence set forth in SEQ ID NO: 16 is a novel acyl-ACP thioesterase derived from *Nannochloropsis pranulata*. The amino acid sequence of the $126^{th}$ to $285^{th}$ amino acids set forth in SEQ ID NO: 16 has about 90% identity with the amino acid sequence of the $115^{th}$ to $274^{th}$ amino acids set forth in SEQ ID NO: 1.

Recombinant proteins at least having the amino acid sequence of the $128^{th}$ to $287^{th}$ amino acids set forth in SEQ ID NO: 14 or the amino acid sequence of the $126^{th}$ to $285^{th}$ amino acids set forth in SEQ ID NO: 16 act as an acyl-ACP thioesterase as demonstrated by the working examples below.

The protein (b) is preferably the protein (a1) or (a2).

Further, the protein (b) is also preferably a protein consisting of an amino acid sequence of the protein (a) in which one or several amino acids (preferably 1 or more and 10 or less amino acids, more preferably 1 or more and 5 or less amino acids, and further preferably 1 or more and 3 or less amino acids) are mutated.

Further, the protein (b) is also preferably a protein consisting of an amino acid sequence of the protein (a1) in which one or several amino acids (preferably 1 or more and 10 or less amino acids, more preferably 1 or more and 5 or less amino acids, and further preferably 1 or more and 3 or less amino acids) are mutated.

Further, the protein (b) is also preferably a protein consisting of an amino acid sequence of the protein (a2) in which one or several amino acids (preferably 1 or more and 10 or less amino acids, more preferably 1 or more and 5 or less amino acids, and further preferably 1 or more and 3 or less amino acids) are mutated.

The above amino acid mutation includes deletion, substitution, insertion or addition of amino acids.

A method of introducing the mutation into an amino acid sequence includes a method of, for example, introducing mutations into a nucleotide sequence encoding the amino acid sequence. The method of introducing mutations into a nucleotide sequence is described later.

The protein (c) contains an amino acid sequence of the protein (a) or (b) as part of the amino acid sequence thereof. Among the amino acid sequence composing the protein (c), specific examples of sequences other than the amino acid sequences of the protein (a) or (b) include an arbitrary portion of the amino acid sequence set forth in SEQ ID NO: 1 other than the amino acid sequence of the $115^{th}$ to $274^{th}$ amino acids set forth in SEQ ID NO: 1, an arbitrary portion of the amino acid sequence set forth in SEQ ID NO: 14 other than the amino acid sequence of the $128^{th}$ to $287^{th}$ amino acids set forth in SEQ ID NO: 14, an arbitrary portion of the amino acid sequence set forth in SEQ ID NO: 16 other than the amino acid sequence of the $126^{th}$ to $285^{th}$ amino acids set forth in SEQ ID NO: 16, and an amino acid sequence in which one or several amino acids (preferably 1 or more and 10 or less amino acids, more preferably 1 or more and 5 or less amino acids, and further preferably 1 or more and 3 or less amino acids) are mutated in these sequences. The above amino acid mutation includes deletion, substitution, insertion or addition of amino acid.

The protein (c) is preferably a protein containing the amino acid sequence of the protein (a), a protein containing the amino acid sequence of the protein (a1), a protein containing the amino acid sequence of the protein (a2), or a protein containing an amino acid sequence of any one of the proteins (a), (a1) and (a2), in which one or several amino acids (preferably 1 or more and 10 or less amino acids, more preferably 1 or more and 5 or less amino acids, and further preferably 1 or more and 3 or less amino acids) are mutated.

Further, as the protein (c), a protein consisting of an amino acid sequence of the $36^{th}$ to $274^{th}$ amino acids set forth in SEQ ID NO: 1, a protein consisting of an amino acid sequence of the $45^{th}$ to $274^{th}$ amino acids set forth in SEQ ID NO: 1, a protein consisting of an amino acid sequence of the $55^{th}$ to $274^{th}$ amino acids set forth in SEQ ID NO: 1, a protein consisting of an amino acid sequence of the $65^{th}$ to $274^{th}$ amino acids set forth in SEQ ID NO: 1, a protein consisting of an amino acid sequence of the $75^{th}$ to $274^{th}$ amino acids set forth in SEQ ID NO: 1, a protein consisting of an amino acid sequence of the $85^{th}$ to $274^{th}$ amino acids set forth in SEQ ID NO: 1, a protein consisting of an amino acid sequence of the $95^{th}$ to $274^{th}$ amino acids set forth in SEQ ID NO: 1, and a protein consisting of an amino acid sequence of the $105^{th}$ to $274^{th}$ amino acids set forth in SEQ ID NO: 1 are more preferable. Further, a protein consisting of any one of these amino acid sequences, in which one or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and particularly preferably 1 or more and 3 or less amino acids) are mutated, is also preferable. These proteins are confirmed to have the acyl-ACP thioesterase activity by Examples described later.

Further, as the protein (c), a protein consisting of an amino acid sequence set forth in SEQ ID NO: 14, a protein consisting of an amino acid sequence of the $49^{th}$ to $287^{th}$ amino acids set forth in SEQ ID NO: 14, a protein consisting of an amino acid sequence of the $58^{th}$ to $287^{th}$ amino acids set forth in SEQ ID NO: 14, a protein consisting of an amino acid sequence of the $78^{th}$ to $287^{th}$ amino acids set forth in SEQ ID NO: 14, a protein consisting of an amino acid sequence of the $88^{th}$ to $287^{th}$ amino acids set forth in SEQ ID NO: 14, a protein consisting of an amino acid sequence of the $98^{th}$ to $287^{th}$ amino acids set forth in SEQ ID NO: 14, a protein consisting of an amino acid sequence of the $108^{th}$ to $287^{th}$ amino acids set forth in SEQ ID NO: 14, a protein consisting of an amino acid sequence of the $118^{th}$ to $287^{th}$ amino acids set forth in SEQ ID NO: 14, and a protein consisting of any one of these amino acid sequences, in which one or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and particularly preferably 1 or more and 3 or less amino acids) are mutated, are more preferable.

Further, as the protein (c), a protein consisting of an amino acid sequence set forth in SEQ ID NO: 16, a protein consisting of an amino acid sequence of the $35^{th}$ to $285^{th}$ amino acids set forth in SEQ ID NO: 16, a protein consisting of an amino acid sequence of the $55^{th}$ to $285^{th}$ amino acids set forth in SEQ ID NO: 16, a protein consisting of an amino acid sequence of the $85^{th}$ to $285^{th}$ amino acids set forth in SEQ ID NO: 16, and a protein consisting of any one of these amino acid sequences, in which one or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and particularly preferably 1 or more and 3 or less amino acids) are mutated, are more preferable.

The above amino acid mutation includes deletion, substitution, insertion or addition of amino acid.

Moreover, the protein (c) also preferably includes a protein consisting of an amino acid sequence formed such that a signal peptide engaging in transport or secretion of the protein is added to the amino acid sequence of the protein (a) or (b). Specific examples of addition of the signal peptide include addition to an N terminus of chloroplast transit peptide.

The acyl-ACP thioesterase activity of the protein of the present invention can be measured by, for example, introducing a fusion gene produced by linking the acyl-ACP thioesterase gene to the downstream of a promoter which functions in a host cell such as *Escherichia coli*, into a host cell which lacks a fatty acid degradation system, culturing the thus-obtained cell under the conditions suitable for the expression of the introduced acyl-ACP thioesterase gene, and analyzing any change caused thereby in the fatty acid composition of the cell or the cultured liquid by using a gas chromatographic analysis or the like.

Alternatively, the acyl-ACP thioesterase activity can be measured by introducing a fusion gene produced by linking the acyl-ACP thioesterase gene to the downstream of a promoter which functions in a host cell such as *Escherichia coli*, into a host cell, culturing the thus-obtained cell under the conditions suitable for the expression of the introduced acyl-ACP thioesterase gene, and subjecting a disruption liquid of the cell to a reaction which uses acyl-ACPs, as substrates, prepared according to the method of Yuan (Yuan L, Voelker T A, Hawkins D J. "Modification of the substrate specificity of an acyl-acyl carrier protein thioesterase by protein engineering", Proc. Natl. Acad. Sci. U.S.A., 1995 Nov. 7; 92 (23), p. 10639-10643).

There are no particular limitations on the method for obtaining the protein of the present invention, and the protein may be obtained by chemical techniques or genetic engineering techniques that are ordinarily carried out. For example, a natural product-derived protein can be obtained through isolation, purification and the like from *Nannochloropsis gaditana*. Furthermore, the protein can also be artificially synthesized based on the information for the amino acid sequence set forth in SEQ ID NO: 1, and protein synthesis may be carried out by chemical synthesis, or a recombinant protein may also be produced by gene recombination technologies. In the case of producing a recombinant protein, the acyl-ACP thioesterase gene of the present invention described below can be used.

2. Acyl-ACP Thioesterase Gene

The gene of the present invention is a gene encoding any one of the proteins (a) to (c).

Specific examples of the gene encoding any one of the proteins (a) to (c) include a gene consisting of any one of DNAs (d) to (f) as follows:

(d) A DNA consisting of a nucleotide sequence of the $343^{rd}$ to $825^{th}$ nucleotides set forth in SEQ ID NO: 2;

(e) A DNA consisting of a nucleotide sequence having 50% or more identity with the nucleotide sequence of the DNA (d), and encoding a protein having acyl-ACP thioesterase activity; and (f) A DNA containing the nucleotide sequence of the DNA (d) or (e), and encoding a protein having acyl-ACP thioesterase activity.

In the DNA (e), the sequence identity of nucleotide sequence is preferably 60% or more, more preferably 70% or more, further preferably 80% or more, further more preferably 90% or more, and particularly preferably 95% or more, in view of acyl-ACP thioesterase activity. The sequence identity of nucleotide sequence can be calculated through the method described above.

Specific examples of the DNA (e) include the following DNA (d1) or (d2).

(d1) A DNA consisting of a nucleotide sequence of the $382^{nd}$ to $864^{th}$ nucleotides set forth in SEQ ID NO: 15.

(d2) A DNA consisting of a nucleotide sequence of the $376^{th}$ to $858^{th}$ nucleotides set forth in SEQ ID NO: 17.

The nucleotide sequence set forth in SEQ ID NO: 15 is a gene encoding a novel acyl-ACP thioesterase derived from *Nannochloropsis oculata*. The nucleotide sequence of the $382^{nd}$ to $864^{th}$ nucleotides set forth in SEQ ID NO: 15 has about 76% identity with the nucleotide sequence of the $343^{rd}$ to $825^{th}$ nucleotides set forth in SEQ ID NO: 2.

The nucleotide sequence set forth in SEQ ID NO: 17 is a gene encoding a novel acyl-ACP thioesterase derived from *Nannochloropsis granulata*. The nucleotide sequence of the $376^{th}$ to $858^{th}$ nucleotides set forth in SEQ ID NO: 17 has about 75% identity with the nucleotide sequence of the $343^{rd}$ to $825^{th}$ nucleotides set forth in SEQ ID NO: 2.

The DNA (e) is preferably the DNA (d1) or (d2).

Further, the DNA (e) is also preferably a DNA consisting of a nucleotide sequence of the DNA (d) in which one or several nucleotides (preferably 1 or more and 10 or less nucleotides, more preferably 1 or more and 5 or less nucleotides, and further preferably 1 or more and 3 or less nucleotides) are mutated.

Further, the DNA (e) is also preferably a DNA consisting of a nucleotide sequence of the DNA (d1) in which one or several nucleotides (preferably 1 or more and 10 or less nucleotides, more preferably 1 or more and 5 or less nucleotides, and further preferably 1 or more and 3 or less nucleotides) are mutated.

Further, the DNA (e) is also preferably a DNA consisting of a nucleotide sequence of the DNA (d2) in which one or several nucleotides (preferably 1 or more and 10 or less nucleotides, more preferably 1 or more and 5 or less nucleotides, and further preferably 1 or more and 3 or less nucleotides) are mutated.

The above nucleotide mutation includes deletion, substitution, insertion or addition of nucleotide.

A method of introducing the mutation into a nucleotide sequence includes a method of introducing a site-specific mutation. Examples of the method of introducing the site-specific mutation include a method of utilizing the splicing overlap extension (SOE) PCR (Horton et al., Gene 77, 61-68, 1989), the ODA method (Hashimoto-Gotoh et al., Gene, 152, 271-276, 1995), and the Kunkel method (Kunkel, T. A., Proc. Natl. Acad. Sci. USA, 1985, 82, 488). Further, commercially available kits such as Site-Directed Mutagenesis System Mutan-SuperExpress Km kit (manufactured by Takara Bio, Inc.), Transformer TM Site-Directed Mutagenesis kit (manufactured by Clonetech Laboratories, Inc.), and KOD-Plus-Mutagenesis kit (manufactured by Toyobo Co., Ltd.) can also be utilized. Furthermore, a gene containing a desired mutation can also be obtained by introducing a genetic mutation at random, and then performing an evaluation of the enzyme activities and a gene analysis thereof by an appropriate method.

The DNA (f) contains a nucleotide sequence of the DNA (d) or (e) as part of the nucleotide sequence thereof. Among the nucleotide sequence composing the DNA (f), specific examples of sequences other than the nucleotide sequence of the DNA (d) or (e) include an arbitrary portion of the nucleotide sequence set forth in SEQ ID NO: 2 other than the nucleotide sequence of the $343^{rd}$ to $825^{th}$ nucleotides set forth in SEQ ID NO: 2, an arbitrary portion of the nucleotide sequence set forth in SEQ ID NO: 15 other than the nucleotide sequence of the $382^{nd}$ to $864^{th}$ nucleotides set forth in SEQ ID NO: 15, an arbitrary portion of the nucleotide sequence set forth in SEQ ID NO: 17 other than the nucleotide sequence of the $376^{th}$ to $858^{th}$ nucleotides set forth in SEQ ID NO: 17, and a nucleotide sequence in which one or several nucleotides (preferably 1 or more and 10 or less nucleotides, more preferably 1 or more and 5 or less nucleotides, and further preferably 1 or more and 3 or less nucleotides) are mutated in these sequences. The above nucleotide mutation includes deletion, substitution, insertion or addition of nucleotide.

The DNA (f) is preferably a DNA containing the nucleotide sequence of the DNA (d), a DNA containing the nucleotide sequence of the DNA (d1), a DNA containing the nucleotide sequence of the DNA (d2), or a DNA containing a nucleotide sequence of any one of the DNAs (d), (d1) and (d2), in which one or several nucleotides (preferably 1 or more and 10 or less nucleotides, more preferably 1 or more and 5 or less nucleotides, and further preferably 1 or more and 3 or less nucleotides) are mutated.

Further, as the DNA (f), a DNA consisting of a nucleotide sequence of the $106^{th}$ to $825^{th}$ nucleotides set forth in SEQ ID NO: 2, a DNA consisting of a nucleotide sequence of the $133^{rd}$ to $825^{th}$ nucleotides set forth in SEQ ID NO: 2, a DNA consisting of a nucleotide sequence of the $163^{rd}$ to $825^{th}$ nucleotides set forth in SEQ ID NO: 2, a DNA consisting of a nucleotide sequence of the $193^{rd}$ to $825^{th}$ nucleotides set forth in SEQ ID NO: 2, a DNA consisting of a nucleotide sequence of the $223^{rd}$ to $825^{th}$ nucleotides set forth in SEQ ID NO: 2, a DNA consisting of a nucleotide sequence of the $253^{rd}$ to $825^{th}$ nucleotides set forth in SEQ ID NO: 2, a DNA consisting of a nucleotide sequence of the $283^{rd}$ to $825^{th}$ nucleotides set forth in SEQ ID NO: 2, and a DNA consisting of a nucleotide sequence of the $313^{rd}$ to $825^{th}$ nucleotides set forth in SEQ ID NO: 2 are more preferable. Further, a DNA consisting of any one of these nucleotide sequences, in which one or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and particularly preferably 1 or more and 3 or less nucleotides) are mutated, is also preferable. The proteins encoded by these DNAs are confirmed to have the acyl-ACP thioesterase activity by Examples described later.

Further, as the DNA (f), a DNA consisting of a nucleotide sequence set forth in SEQ ID NO: 15, a DNA consisting of a nucleotide sequence of the $145^{th}$ to $864^{th}$ nucleotides set forth in SEQ ID NO: 15, a DNA consisting of a nucleotide sequence of the $172^{nd}$ to $864^{th}$ nucleotides set forth in SEQ ID NO: 15, a DNA consisting of a nucleotide sequence of the $232^{nd}$ to $864^{th}$ nucleotides set forth in SEQ ID NO: 15, a DNA consisting of a nucleotide sequence of the $262^{nd}$ to $864^{th}$ nucleotides set forth in SEQ ID NO: 15, a DNA consisting of a nucleotide sequence of the $292^{nd}$ to $864^{th}$ nucleotides set forth in SEQ ID NO: 15, a DNA consisting of a nucleotide sequence of the $322^{nd}$ to $864^{th}$ nucleotides set forth in SEQ ID NO: 15, a DNA consisting of a nucleotide sequence of the $352^{nd}$ to $864^{th}$ nucleotides set forth in SEQ ID NO: 15, and a DNA consisting of any one of these nucleotide sequences, in which one or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and particularly preferably 1 or more and 3 or less nucleotides) are mutated, are more preferable.

Further, as the DNA (f), a DNA consisting of a nucleotide sequence set forth in SEQ ID NO: 17, a DNA consisting of a nucleotide sequence of the $103^{rd}$ to $858^{th}$ nucleotides set forth in SEQ ID NO: 17, a DNA consisting of a nucleotide sequence of the $163^{rd}$ to $858^{th}$ nucleotides set forth in SEQ ID NO: 17, a DNA consisting of a nucleotide sequence of the $253^{rd}$ to $858^{th}$ nucleotides set forth in SEQ ID NO: 17, and a DNA consisting of any one of these nucleotide sequences, in which one or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and particularly preferably 1 or more and 3 or less nucleotides) are mutated, are more preferable.

The above nucleotide mutation includes deletion, substitution, insertion or addition of nucleotide.

Moreover, the DNA (f) also preferably includes a DNA consisting of a nucleotide sequence formed such that a nucleotide sequence encoding a signal peptide engaging in transport or secretion of the protein is added to the nucleotide sequence of the protein (d) or (e). Specific examples of the signal peptide to be added thereto include the proteins described in the protein (c).

A method of obtaining the acyl-ACP thioesterase gene of the present invention is not particularly limited, and the thioesterase gene can be obtained by ordinary genetic engineering techniques. For example, the thioesterase gene of the present invention can be obtained by artificial synthesis based on the amino acid sequence set forth in SEQ ID NO: 1 or the nucleotide sequence set forth in SEQ ID NO: 2. The artificial synthesis of a gene can be achieved by utilizing the services such as Invitrogen, Inc. Furthermore, the gene can also be obtained by cloning from *Nannochloropsis gaditana*. The cloning can be carried out by, for example, the methods described in Molecular Cloning—A LABORATORY MANUAL THIRD EDITION [Joseph Sambrook, David W. Russell, Cold Spring Harbor Laboratory Press (2001)] and the like.

3. Transformant (1) First Embodiment

The transformant of the first embodiment of the present invention is obtained by introducing the acyl-ACP thioesterase gene of the present invention or a recombinant vector containing the gene into a host.

The introduction of the acyl-ACP thioesterase gene into a host can be carried out according to an ordinary genetic engineering method. Specifically, the transformant can be produced by preparing a vector capable of expressing the acyl-ACP thioesterase gene of the present invention in a host cell, introducing this vector into a host cell to transform the host cell.

The host cell used for the transformant is not particularly limited, and examples of the host cell include microorganisms, plants or animals. In the present invention, microorganisms include microalgae. Among these, microorganisms and plants are preferable, and microorganisms are more preferable, from the viewpoints of production efficiency and the usability of lipids.

As the microorganisms for the host cell, prokaryotes and eukaryotes can be used. Prokaryotes include microorganisms which belong to the genus *Escherichia* or microorganisms which belong to the genus *Bacillus*. Eukaryotes include yeast or filamentous fungi. Among them, from the viewpoint of the productivity of lipids, *Escherichia coli*, *Bacillus subtilis*, *Rhodosporidium toruloides*, and *Mortierella* sp. are preferable, and *Escherichia coli* is more preferable.

As the microorganisms for the host cell, microalgae are also preferable. As microalgae, from a viewpoint of establishment of a gene recombination technique, algae belonging to the genus *Chlamydomonas*, algae belonging to the genus *Chlorella*, algae belonging to the genus *Phaeodactylum*, and algae belonging to the genus *Nannochloropsis* are preferable, and algae belonging to the genus *Nannochloropsis* are more preferable. Specific examples of the algae belonging to the genus *Nannochloropsis* include *Nannochloropsis oculata*, *Nannochloropsis paditana*, *Nannochloropsis salina*, *Nannochloropsis oceanica*, *Nannochloropsis atomus*, *Nannochloropsis maculata*, *Nannochloropsis granulata*, and *Nannochloropsis* sp. Among them, from the viewpoint of the productivity of lipids, *Nannochloropsis oculata* or *Nannochloropsis qaditana* is preferable, and *Nannochloropsis oculata* is more preferable.

As the plants for the host cell, from the viewpoint of a lipid content of seeds, *Arabidopsis thaliana*, rapeseed, *Cocos nucifera*, palm, cuphea, and *Jatropha curcas* are preferable, and *Arabidopsis thaliana* is more preferable.

A vector for use as the expression vector may be any vector capable of introducing the acyl-ACP thioesterase gene of the present invention into a host cell, and expressing the gene in the host cell. For example, a vector which has expression regulation regions such as a promoter and a terminator in accordance with the type of the host cell to be used, and has a replication initiation point, a selection marker or the like, can be used. Furthermore, the vector may also be a vector capable of self-proliferation and self-replication outside the chromosome, such as a plasmid, or may also be a vector which is incorporated into the chromosome.

Specific examples of the vector include, in the case of using a microorganism as the host cell, pBluescript II SK(−) (manufactured by Stratagene Corp.), pUC-based vector (manufactured by Takara Shuzo Co., Ltd.), a pET-based vector (manufactured by Takara Bio, Inc.), a pGEX-based vector (manufactured by GE Healthcare, Inc.), a pCoid-based vector (manufactured by Takara Bio, Inc.), pHY300PLK (manufactured by Takara Bio, Inc.), pUB110 (Mckenzie, T. et al., (1986), Plasmid 15(2); p. 93-103), pBR322 (manufactured by Takara Bio, Inc.), pRS403 (manufactured by Stratagene Corp.), and pMW218/219 (manufactured by Nippon Gene Co., Ltd.). Particularly, in the case of using *Escherichia coli* as the host cell, pBluescript II SK(−) or pMW218/219 is preferably used.

When the algae is used as the host cell, specific examples of the vector include P66 (*Chlamydomonas* Center), P-322 (*Chlamydomonas* Center), pPha-T1 (see Non-Patent Literature 2 described above) and pJET1 (manufactured by COSMO BIO co., ltd.). In particular, in the case of using the algae belonging to the genus *Nannochloropsis* as the host cell, pPha-T1 or pJET1 is preferably used. Moreover, when the host cell is the algae belonging to the genus *Nannochloropsis*, the host cell can be transformed, with referring to the method described in the literature, Oliver Kilian, et al., Proceedings of the National Academy of Sciences of the United States of America, December 27; 108(52), 2011, by using the DNA fragment consisting of the gene of the present invention, a promoter and a terminator. Specific examples of this DNA fragment include a PCR-amplified DNA fragment and a restriction enzyme-cut DNA fragment.

In the case of using a plant cell as the host cell, examples of the vector include a pRI-based vector (manufactured by Takara Bio, Inc.), a pBI-based vector (manufactured by Clontech Laboratories, Inc.), and an IN3-based vector (manufactured by Inplanta Innovations, Inc.). Particularly, in the case of using *Arabidopsis thaliana* as the host cell, a pRI-based vector or a pBI-based vector is preferably used.

The expression regulation regions such as a promoter and a terminator, and the selection marker are not particularly limited, and can be appropriately selected from ordinarily used promoters, markers and the like in accordance with the type of the host cell to be used.

Specific examples of the promoter include lac promoter, trp promoter, tac promoter, trc promoter, T7 promoter, SpoVG promoter, cauliflower mosaic virus 35S RNA promoter, promoters for housekeeping genes such as tubulin, actin and ubiquitin, rapeseed-derived Napin gene promoter, plant-derived Rubisco promoter, and a promoter of a violaxanthin/(chlorophyll a)-binding protein gene derived from the genus *Nannochloropsis*.

Examples of the selection marker include drug resistance genes such as antibiotic resistance genes (e.g. an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene). Further, it is also possible to use a deletion of an auxotrophy-related gene or the like as the selection marker.

A vector for transformation can be constructed by introducing the acyl-ACP thioesterase gene of the present invention into the above-described vector according to an ordinary technique such as restriction enzyme treatment or ligation.

The method for transformation is not particularly limited as long as it is a method capable of introducing a target gene into a host cell. For example, a method of using calcium ion, a general competent cell transformation method (J. Bacterial. 93, 1925 (1967)), a protoplast transformation method (Mol. Gen. Genet. 168, 111 (1979)), an electroporation method (FEMS Microbiol. Lett. 55, 135 (1990)), an LP transformation method (T. Akamatsu and J. Sekiguchi, Archives of Microbiology, 1987, 146, p. 353-357; T. Akamatsu and H. Taguchi, Bioscience, Biotechnology, and Biochemistry, 2001, 65, 4, p. 823-829) and the like, can be used. When the host is the algae belonging to the genus *Nannochloropsis*, transformation can also be performed by applying the electroporation method described in Randor Radakovits, et al., Nature Communications, DO1:10.1038/ncomms1688, 2012.

The selection of a transformant having a target gene fragment introduced therein can be carried out by using the selection marker or the like. For example, the selection can be carried out by using an indicator whether a transformant acquires the drug resistance as a result of introducing a vector-derived drug resistance gene into a host cell together with a target DNA fragment. Further, the introduction of a target DNA fragment can also be confirmed by PCR using a genome as a template.

The transformant of the present embodiment can efficiently produce a fatty acid having a specific number of carbon atoms (chain length) and unsaturated bonds, and can produce improved amount of lipids. The ability to produce fatty acids of the transformant can be measured by the method used in the Examples.

(2) Second Embodiment

The transformant of the second embodiment of the present invention is a transformant in which, in a host cell having the acyl-ACP thioesterase gene of the present invention, the gene is subjected to deletion, mutation or repression of gene expression. The transformant can be obtained by deleting, mutating or repressing the acyl-ACP thioesterase gene of the present invention in the host cell.

The host cell of the transformant of this embodiment only needs to have the acyl-ACP thioesterase gene of the present invention. For example, microorganisms, plants or animals can be used as the host cell. Among these, microorganisms are preferable, and microalgae are more preferable, from the viewpoint of the productivity of lipids.

As the microalgae, from the viewpoint of the productivity of lipids, algae belonging to the genus *Nannochloropsis* are preferable. Specific examples of the algae belonging to the genus *Nannochloropsis* include *Nannochloropsis oculata, Nannochloropsis gaditana, Nannochloropsis salina, Nannochloropsis oceanica, Nannochloropsis atomus, Nannochloropsis maculata, Nannochloropsis granulata,* and *Nannochloropsis sp.* Among them, from the viewpoint of the productivity of lipids, *Nannochloropsis oculata* or *Nannochloropsis gaditana* is preferable, and *Nannochloropsis oculata* is more preferable.

The deletion, mutation or repression of the acyl-ACP thioesterase gene of the present invention from a host genome can be conducted by a method of partially or wholly removing a target gene from a genome, replacing the target gene by other genes, inserting other DNA fragments into the target gene, or providing mutation in an active site, a substrate-binding site, or a transcription or translation initiation region of the target gene.

The above method of deletion, mutation or repression of gene expression can employ homologous recombination techniques. For example, a linear DNA fragment containing an upstream and downstream regions of a target gene in a host genome but containing no target gene is constructed by a method such as PCR, and the resultant DNA fragment is incorporated into a host cell to cause double crossover homologous recombination on the side upstream and downstream of the target gene of the host genome, and then the target gene on the genome can be deleted or substituted for other gene fragment. Moreover, a target gene into which mutation such as nucleotide substitution and nucleotide insertion is introduced is constructed by a method such as PCR, and the resulting gene is incorporated into a host cell to cause double crossover homologous recombination in two regions outside the mutation site in the target gene of the host genome, and then a function of the target gene on the genome can be deteriorated or lost. Moreover, a cyclic recombinant plasmid is prepared by introducing a DNA fragment partially containing a target gene into a suitable plasmid vector, and the resultant plasmid is incorporated into a host cell to cause homologous recombination in part of region of the target gene on the host genome and to split the target gene of the host genome, and then a function of the target gene can be deteriorated or lost.

The method of deletion, mutation or repression of gene expression of a target gene using homologous recombination can be conducted with reference to literature such as Besher et al., Methods in molecular biology 47, pp. 291-302, 1995. In particular, when the host cell is the algae belonging to the genus *Nannochloropsis*, with referring to the literature such as Oliver Kilian, et al., Proceedings of the National Academy of Sciences of the United States of America, December 27; 108(52), 2011, a specific gene in the genome can be deleted or disrupted by a homologous recombination method.

The selection of transformants with deletion or the like of the target gene can be made by a method of extracting genome DNA from the transformant and performing PCR to amplify a region containing the target gene, a southern blotting method using a DNA probe to be bonded with the target gene region, or the like.

With regard to the transformant of this embodiment, the acyl-ACP thioesterase gene of the present invention does not function. Therefore, the fatty acid composition of the lipid produced is considered to change from the composition original to the host. More specifically, the transformant can produce a lipid in which the fatty acid composition is modified.

4. Method of Producing Lipid

The transformant of the present invention is used for the production method of the present invention. The production method of the present invention contains culturing the transformant in a medium, and collecting a lipid from the resulting cultured product. In the present invention, the culturing of a transformant includes culturing of a microorganism, algae, animal or plant, or a cell or tissue thereof, and also cultivating of a plant in soil or the like. Moreover, the cultured product includes a medium used for culture, and a transformant subjected to cultivation or the like.

The medium and culture condition can be selected in accordance with the type of the host cell for transformation, and any appropriate preferred medium and condition can be employed. Further, from the viewpoint of the productivity of lipids, substrates for thioesterase or precursor substances participating in the fatty acid biosynthesis, such as glycerol, acetic acid or malonic acid, may be added to the medium.

For instance, in the case of using *Escherichia coli* as the host cell for transformation, culture may be carried out in LB medium or Overnight Express Instant TB Medium (manufactured by Novagen, Inc.) at 30° C. to 37° C. for half a day to 1 day. In the case of using *Arabidopsis thaliana* as the host cell for transformation, growth may be carried out under the temperature conditions of 20° C. to 25° C., by continuously irradiating white light or under white light illumination conditions of a light period of 16 hours and a dark period of 8 hours, for one to two months.

When the host cell of the transformation is the algae, the following culture media and culture conditions can be applied.

As the culture medium, a medium based on natural seawater or artificial seawater may be used. Alternatively, a commercially available culture medium may also be used. Specific examples of the culture medium include an f/2 medium, an ESM medium, a Daigo IMK medium, an L1 medium and an MNK medium. Above all, from viewpoints of an improvement in the productivity of lipids and a nutritional ingredient concentration, an f/2 medium, an ESM medium or a Daigo IMK medium is preferred, an f/2 medium or a Daigo IMK medium is more preferred, and an f/2 medium is further preferred. For growth promotion of the algae and an improvement in productivity of a medium chain fatty acid, a nitrogen source, a phosphorus source, a metal salt, vitamins, a trace metal or the like can be appropriately added to the culture medium.

An amount of the algae to be seeded to the culture medium is not particularly limited. In view of viability, the amount is preferably 1% to 50% (vol/vol), and more preferably 1% to 10% (vol/vol), per culture medium. Culture temperature is not particularly limited within the range in which the temperature does not adversely affect growth of the algae, but is ordinarily in the range of 5° C. to 40° C. From viewpoints of the growth promotion of the algae, the improvement in productivity of a medium chain fatty acid, and reduction of production cost, the temperature is preferably 10° C. to 35° C., and more preferably 15° C. to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of a medium chain fatty acid, irradiance during the light irradiation is preferably in the range of 100 lx to 50,000 lx, more preferably in the range of 300 to 10,000 lx, and further preferably 1,000 lx to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably 8 of 24 hours, further preferably 10 to 18 hours, and still further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From the viewpoints of the growth promotion or the improvement in the productivity of a medium chain fatty acid, the concentration is preferably 0.03% (which is the same degree as the concentration under atmospheric conditions) to 10%, more preferably 0.05% to 5%, further preferably 0.1% to 3%, and still further preferably 0.3% to 1%. A concentration of the carbonate is not particularly limited. When the sodium hydrogen carbonate is used, for example, from the viewpoints of the growth promotion and the improvement in the productivity of a medium chain fatty acid, the concentration is preferably 0.01 to 5% by mass, more preferably 0.05 to 2% by mass, and further preferably 0.1 to 1% by mass.

A culture time is not particularly limited, and the culture may be performed for a long time (for example, about 150 days) so that an alga body in which the lipid is accumulated at a high concentration can grow at a high concentration. From the viewpoints of the growth promotion of the algae, the improvement in the productivity of a medium chain fatty acid, and the reduction of production cost, a culture time is preferably 3 to 90 days, more preferably 3 to 30 days, and further preferably 7 to 30 days. In addition, the culture may be performed in any of aerated and agitated culture, shaking culture or static culture. From a viewpoint of improving air-permeability, shaking culture is preferred.

Lipids produced in the transformant is isolated or collected by an ordinary method used for isolating lipid components and the like. For example, lipid components can be isolated and collected from the cultured product or transformant by means of filtration, centrifugation, cell disruption, gel filtration chromatography, ion exchange chromatography, chloroform/methanol extraction, hexane extraction, ethanol extraction, or the like. In the case of isolation and collection of larger scales, lipids can be obtained by collecting oil components from the cultured product or transformant through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The production method of the present invention can be preferably used in the production of fatty acids having 8 or more and 22 or less carbon atoms and derivatives thereof. Particularly, the production method of the present invention can be more preferably used in the production of fatty acids having 12 or more and 20 or less carbon atoms and derivatives thereof, more preferably used in the production of fatty acids having 12 or more and 14 or less carbon atoms and derivatives thereof.

The lipids obtained by the production method and the transformant of the present invention can be utilized for food, as well as can be utilized as an emulsifier incorporated into cosmetic products or the like, a cleansing agent such as a soap or a detergent, a fiber treatment agent, a hair conditioning agent, a disinfectant or an antiseptic. Moreover, the lipids can also be used as raw materials of biodiesel fuels.

With regard to the embodiments described above, the present invention also discloses a protein, a gene, a transformant, and a method described below.

<1> A protein selected from the following (a) to (c):
(a) A protein consisting of an amino acid sequence of the 115$^{th}$ to 274$^{th}$ amino acids set forth in SEQ ID NO: 1;
(b) A protein consisting of an amino acid sequence having 50% or more, preferably 60% or more, more preferably 70% or more, further preferably 80% or more, further more preferably 90% or more, and particularly preferably 95% or more identity with the amino acid sequence of the protein (a), and having acyl-ACP thioesterase activity; and
(c) A protein containing the amino acid sequence of the protein (a) or (b), and having acyl-ACP thioesterase activity.

<2> The protein according to the above item <1>, wherein the protein (b) is a protein (a1)) or (a2) as follows:
(a1) A protein consisting of an amino acid sequence of the 128$^{th}$ to 287$^{th}$ amino acids set forth in SEQ ID NO: 14, and
(a2) A protein consisting of an amino acid sequence of the 126$^{th}$ to 285$^{th}$ amino acids set forth in SEQ ID NO: 16.

<3> The protein according to the above item <1>, wherein the protein (b) is a protein consisting of an amino acid sequence of the protein (a), (a1) or (a2) in which one or several amino acids, preferably 1 or more and 10 or less amino acids, more preferably 1 or more and 5 or less amino acids, and further preferably 1 or more and 3 or less amino acids, are mutated, and having acyl-ACP thioesterase activity.

<4> The protein according to the above item <1>, wherein the protein (c) is a protein selected from the group consisting of:
a protein consisting of an amino acid sequence of the 36$^{th}$ to 274$^{th}$ amino acids set forth in SEQ ID NO: 1;
a protein consisting of an amino acid sequence of the 45$^{th}$ to 274$^{th}$ amino acids set forth in SEQ ID NO: 1;
a protein consisting of an amino acid sequence of the 55$^{th}$ to 274$^{th}$ amino acids set forth in SEQ ID NO: 1;
a protein consisting of an amino acid sequence of the 65$^{th}$ to 274$^{th}$ amino acids set forth in SEQ ID NO: 1;
a protein consisting of an amino acid sequence of the 75$^{th}$ to 274$^{th}$ amino acids set forth in SEQ ID NO: 1;
a protein consisting of an amino acid sequence of the 85$^{th}$ to 274$^{th}$ amino acids set forth in SEQ ID NO: 1;
a protein consisting of an amino acid sequence of the 95$^{th}$ to 274$^{th}$ amino acids set forth in SEQ ID NO: 1;
a protein consisting of an amino acid sequence of the 105$^{th}$ to 274$^{th}$ amino acids set forth in SEQ ID NO: 1;
a protein consisting of an amino acid sequence of the 1$^{st}$ to 287$^{th}$ amino acids set forth in SEQ ID NO: 14;
a protein consisting of an amino acid sequence of the 49$^{th}$ to 287$^{th}$ amino acids set forth in SEQ ID NO: 14;
a protein consisting of an amino acid sequence of the 58$^{th}$ to 287$^{th}$ amino acids set forth in SEQ ID NO: 14;

a protein consisting of an amino acid sequence of the 78$^{th}$ to 287$^{th}$ amino acids set forth in SEQ ID NO: 14;
a protein consisting of an amino acid sequence of the 88$^{th}$ to 287$^{th}$ amino acids set forth in SEQ ID NO: 14;
a protein consisting of an amino acid sequence of the 98$^{th}$ to 287$^{th}$ amino acids set forth in SEQ ID NO: 14;
a protein consisting of an amino acid sequence of the 108$^{th}$ to 287$^{th}$ amino acids set forth in SEQ ID NO: 14;
a protein consisting of an amino acid sequence of the 118$^{th}$ to 287$^{th}$ amino acids set forth in SEQ ID NO: 14;
a protein consisting of an amino acid sequence of the 1$^{st}$ to 285$^{th}$ amino acids set forth in SEQ ID NO: 16;
a protein consisting of an amino acid sequence of the 35$^{th}$ to 285$^{th}$ amino acids set forth in SEQ ID NO: 16;
a protein consisting of an amino acid sequence of the 55$^{th}$ to 285$^{th}$ amino acids set forth in SEQ ID NO: 16;
a protein consisting of an amino acid sequence of the 85$^{th}$ to 285$^{th}$ amino acids set forth in SEQ ID NO: 16; and
a protein consisting of any one of these amino acid sequences, in which one or several amino acids (preferably 1 or more and 20 or less amino acids, more preferably 1 or more and 15 or less amino acids, further preferably 1 or more and 10 or less amino acids, furthermore preferably 1 or more and 5 or less amino acids, and particularly preferably 1 or more and 3 or less amino acids) are mutated, and having acyl-ACP thioesterase activity.

<5> The protein according to the above item <3> or <4>, wherein the amino acid mutation is deletion, substitution, insertion or addition of an amino acid.

<6> A gene encoding the protein according to any one of the above items <1> to <5>.

<7> A gene consisting of any one of the following DNAs (d) to (f):
(d) A DNA consisting of a nucleotide sequence of the 343$^{rd}$ to 825$^{th}$ nucleotides set forth in SEQ ID NO: 2;
(e) A DNA consisting of a nucleotide sequence having 50% or more, preferably 60% or more, more preferably 70% or more, further preferably 80% or more, further more preferably 90% or more, and particularly preferably 95% or more identity with the nucleotide sequence of the DNA (d), and encoding a protein having acyl-ACP thioesterase activity; and
(f) A DNA containing the nucleotide sequence of the DNA (d) or (e), and encoding a protein having acyl-ACP thioesterase activity.

<8> The gene according to the above item <7>, wherein the DNA (e) is a DNA (d1) or (d2) as follows:
(d1) A DNA consisting of a nucleotide sequence of the 382$^{nd}$ to 864$^{th}$ nucleotides set forth in SEQ ID NO: 15, and
(d2) A DNA consisting of a nucleotide sequence of the 376$^{th}$ to 858$^{th}$ nucleotides set forth in SEQ ID NO: 17.

<9> The gene according to the above item <7>, wherein the DNA (e) is a DNA consisting of a nucleotide sequence of the DNA (d), (d1) or (d2) in which one or several nucleotides, preferably 1 or more and 10 or less nucleotides, more preferably 1 or more and 5 or less nucleotides, and further preferably 1 or more and 3 or less nucleotides are mutated, and encoding a protein having acyl-ACP thioesterase activity.

<10> The gene according to the above item <7>, wherein the DNA (f) is a DNA selected from the group consisting of:
a DNA consisting of a nucleotide sequence of the 106$^{th}$ to 825$^{th}$ nucleotides set forth in SEQ ID NO: 2;
a DNA consisting of a nucleotide sequence of the 133$^{rd}$ to 825$^{th}$ nucleotides set forth in SEQ ID NO: 2;
a DNA consisting of a nucleotide sequence of the 163$^{rd}$ to 825$^{th}$ nucleotides set forth in SEQ ID NO: 2;
a DNA consisting of a nucleotide sequence of the 193$^{rd}$ to 825$^{th}$ nucleotides set forth in SEQ ID NO: 2;
a DNA consisting of a nucleotide sequence of the 223$^{rd}$ to 825$^{th}$ nucleotides set forth in SEQ ID NO: 2;
a DNA consisting of a nucleotide sequence of the 253$^{rd}$ to 825$^{th}$ nucleotides set forth in SEQ ID NO: 2;
a DNA consisting of a nucleotide sequence of the 283$^{rd}$ to 825$^{th}$ nucleotides set forth in SEQ ID NO: 2;
a DNA consisting of a nucleotide sequence of the 313$^{rd}$ to 825$^{th}$ nucleotides set forth in SEQ ID NO: 2;
a DNA consisting of a nucleotide sequence of the 1$^{st}$ to 864$^{th}$ nucleotides set forth in SEQ ID NO: 15;
a DNA consisting of a nucleotide sequence of the 145$^{th}$ to 864$^{th}$ nucleotides set forth in SEQ ID NO: 15;
a DNA consisting of a nucleotide sequence of the 172$^{nd}$ to 864$^{th}$ nucleotides set forth in SEQ ID NO: 15;
a DNA consisting of a nucleotide sequence of the 232$^{nd}$ to 864$^{th}$ nucleotides set forth in SEQ ID NO: 15;
a DNA consisting of a nucleotide sequence of the 262$^{nd}$ to 864$^{th}$ nucleotides set forth in SEQ ID NO: 15;
a DNA consisting of a nucleotide sequence of the 292$^{nd}$ to 864$^{th}$ nucleotides set forth in SEQ ID NO: 15;
a DNA consisting of a nucleotide sequence of the 322$^{nd}$ to 864$^{th}$ nucleotides set forth in SEQ ID NO: 15;
a DNA consisting of a nucleotide sequence of the 352$^{nd}$ to 864$^{th}$ nucleotides set forth in SEQ ID NO: 15;
a DNA consisting of a nucleotide sequence of the 1$^{st}$ to 858$^{th}$ nucleotides set forth in SEQ ID NO: 17;
a DNA consisting of a nucleotide sequence of the 103$^{rd}$ to 858$^{th}$ nucleotides set forth in SEQ ID NO: 17;
a DNA consisting of a nucleotide sequence of the 163$^{rd}$ to 858$^{th}$ nucleotides set forth in SEQ ID NO: 17;
a DNA consisting of a nucleotide sequence of the 253$^{rd}$ to 858$^{th}$ nucleotides set forth in SEQ ID NO: 17; and
a DNA consisting of any one of these nucleotide sequences, in which one or several nucleotides (preferably 1 or more and 20 or less nucleotides, more preferably 1 or more and 15 or less nucleotides, further preferably 1 or more and 10 or less nucleotides, furthermore preferably 1 or more and 5 or less nucleotides, and particularly preferably 1 or more and 3 or less nucleotides) are mutated, and encoding a protein having acyl-ACP thioesterase activity.

<11> The gene according to the above item <9> or <10>, wherein the nucleotide mutation is deletion, substitution, insertion or addition of a nucleotide.

<12> A recombinant vector containing the gene according to any one of the above items <6> to <11>.

<13> A transformant obtained by introducing the gene according to any one of the above items <6> to <11> or the recombinant vector according to the above item <12> into a host.

<14> A transformant, wherein, in a host having the gene according to any one of the above items <6> to <11>, the gene is subjected to deletion, mutation or repression of gene expression.

<15> The transformant according to the above item <13> or <14>, wherein the host is a microorganism.

<16> The transformant according to the above item <15>, wherein the microorganism is a microalga.

<17> The transformant according to the above item <16>, wherein the microalga is an alga belonging to the genus *Chlamydomonas*, an alga belonging to the genus *Chlorella*, an alga belonging to the genus *Phaeodactylum*, or an alga belonging to the genus *Nannochloropsis*, and preferably an alga belonging to the genus *Nannochloropsis*.

<18> The transformant according to the above item <17>, wherein the alga belonging to the genus *Nannochloropsis* is *Nannochloropsis oculata, Nannochloropsis gaditana, Nannochloropsis salina, Nannochloropsis oceanica, Nannochloropsis atomus, Nannochloropsis maculata, Nannochloropsis qranulata*, or *Nannochloropsis* sp., preferably *Nannochloropsis oculata* or *Nannochloropsis gaditana*, and more preferably *Nannochloropsis oculata*.
<19> The transformant according to the above item <15>, wherein the microorganism is *Escherichia coli*.
<20> A method of producing a lipid, containing steps of:
culturing the transformant according to any one of the above items <13> to <19> in a medium; and
collecting a lipid from the resulting cultured product.
<21> The method of producing a lipid according to the above item <20>, wherein the lipid contains fatty acids having 8 or more and 22 or less carbon atoms, preferably 12 or more and 20 or less carbon atoms, and more preferably 12 or more and 14 or less carbon atoms, and derivatives thereof.
<22> A method of modifying a fatty acid composition in a lipid, containing introducing the gene according to any one of the above items <6> to <11> into a host.
<23> A method of enhancing productivity of a lipid, containing introducing the gene according to any one of the above items <6> to <11> into a host.
<24> A method of modifying a fatty acid composition in a lipid, containing deleting, mutating or repressing the gene according to any one of the above items <6> to <11> in a host.

EXAMPLES

Hereinafter, the present invention will be described more in detail with reference to Examples, but the present invention is not limited thereto.

Example 1. Preparation of *Escherichia coli* Transformant Having Nga07062 Gene, and Production of Lipid by *Escherichia coli* Transformant 1. Preparation of Nga07062 Gene
Information on sequences of total 9052 genes of *Nannochloropsis gaditana* CCMP 526 were acquired from *Nannochloropsis* Genome Project (nannochloropsis.genomeprojectsolutions-databases.com/) provided by Colorado School of Mines and Genome Project Solutions. For an Nga07062 gene (gene consisting of a nucleotide sequence set forth in SEQ ID NO: 2) being one of the genes, a function was identified by the following method.
2. Construction of Plasmid for Nga07062 Gene Expression
The Nga07062 gene was used as a template, and an Nga07062 gene fragment consisting of a nucleotide sequence of the $106^{th}$ to $825^{th}$ nucleotides set forth in SEQ ID NO: 2 was prepared by PCR using a pair of primers set forth in SEQ ID NO: 3 and SEQ ID NO: 4 as shown in Table 1 below. Herein, the gene having the nucleotide sequence set forth in SEQ ID NO: 2 was obtained utilizing customer synthesis service of an artificial gene. Moreover, a plasmid vector pBluescriptII SK(-) (manufactured by Stratagene, Inc.) was used as a template, and the pBluescriptII SK(-) was amplified by PCR using a pair of primers set forth in SEQ ID NOs: 5 and 6 shown in Table 1 below. Then, the resultant was subjected to digestion by restriction enzyme DpnI (manufactured by TOYOBO Co., Ltd.) treatment. These two fragments were purified using a High Pure PCR Product Purification Kit (manufactured by Roche Applied Science Corporation), and then fused using an In-Fusion HD Cloning Kit (manufactured by Clontech, Inc.) to construct a plasmid Nga07062_106 for Nga07062 gene expression. This expression plasmid was constructed in the form of removing an amino acid sequence of the $1^{st}$ to $35^{th}$ amino acids on a side of an N-terminus of an amino acid sequence (SEQ ID NO: 1) encoded by the Nga07062 gene, and fusing with an amino acid sequence of the $1^{st}$ to $29^{th}$ amino acids on a side of an N-terminus of a LacZ protein derived from the plasmid.

The Nga07062 gene consisting of a nucleotide sequence set forth in SEQ ID NO: 2 was used a template, and PCR was carried out by using pairs of any one of primers set forth in SEQ ID NOs: 7 to 13, and a primer set forth in SEQ ID NO: 4, shown in Table 1 below, to prepare an Nga07062 gene fragment consisting of a nucleotide sequence of the $163^{rd}$ to $825^{th}$ nucleotides set forth in SEQ ID NO: 2, an Nga07062 gene fragment consisting of a nucleotide sequence of the $193^{rd}$ to $825^{th}$ nucleotides set forth in SEQ ID NO: 2, an Nga07062 gene fragment consisting of a nucleotide sequence of the $223^{rd}$ to $825^{th}$ nucleotides set forth in SEQ ID NO: 2, an Nga07062 gene fragment consisting of a nucleotide sequence of the $253^{rd}$ to $825^{th}$ nucleotides set forth in SEQ ID NO: 2, an Nga07062 gene fragment consisting of a nucleotide sequence of the $283^{rd}$ to $825^{th}$ nucleotides set forth in SEQ ID NO: 2, an Nga07062 gene fragment consisting of a nucleotide sequence of the $313^{rd}$ to $825^{th}$ nucleotides set forth in SEQ ID NO: 2, and an Nga07062 gene fragment consisting of a nucleotide sequence the $343^{rd}$ to $825^{th}$ nucleotides set forth in SEQ ID NO: 2, respectively.

Each of the resultant gene fragments was fused with the pBluescriptII SK(-) vector in a manner similar to the method described above to construct a plasmid Nga07062_163 for Nga07062 gene expression, a plasmid Nga07062_193 therefor, a plasmid Nga07062_223 therefor, a plasmid Nga07062_253 therefor, a plasmid Nga07062_283 therefor, a plasmid Nga07062_313 therefor, and a plasmid Nga07062_343 therefor, respectively. Herein, these expression plasmids were constructed in the form of removing amino acid sequences of the $1^{st}$ to $54^{th}$ amino acids, the $1^{st}$ to $64^{th}$ amino acids, the $1^{st}$ to $74^{th}$ amino acids, the $1^{st}$ to $84^{th}$ amino acids, the $1^{st}$ to $94^{th}$ amino acids, the $1^{st}$ to $104^{th}$ amino acids or the $1^{st}$ to $114^{th}$ amino acids on the side of the N-terminus of the amino acid sequence (SEQ ID NO: 1) encoded by the Nga07062 gene, respectively, and fusing with the amino acid sequence of the $1^{st}$ to $29^{th}$ amino acids on the side of the N-terminus of the LacZ protein derived from the plasmid.

TABLE 1

| Nucleotide Sequence of Primers |
| --- |
| SEQ ID NO: 3 GCGGCCGCTCTAGAGCCGGCCCGAGCACTCAGCCATC |
| SEQ ID NO: 4 ACAAAATATTAACGCCTAACTGATGTCCACCTTCTTC |
| SEQ ID NO: 5 CTCTAGAGCGGCCGCCACCG |
| SEQ ID NO: 6 GCGTTAATATTTTGTTAAAATTCG |
| SEQ ID NO: 7 GCGGCCGCTCTAGAGTCATCCTTCTCGATCTTGTTG |
| SEQ ID NO: 8 GCGGCCGCTCTAGAGGTAGCAGGATCATTCGTCGG |
| SEQ ID NO: 9 GCGGCCGCTCTAGAGATCGCTGGGCATACAGCAGG |
| SEQ ID NO: 10 GCGGCCGCTCTAGAGGATGAAGTAAAGTCTCCGCAG |

TABLE 1-continued

Nucleotide Sequence of Primers

SEQ ID NO: 11 GCGGCCGCTCTAGAGAATGTAGGAGGCGGCGCCCAG

SEQ ID NO: 12 GCGGCCGCTCTAGAGCCCTACACGGTCACTTTTGC

SEQ ID NO: 13 GCGGCCGCTCTAGAGCATGATCGAGTGGACACAAAAC

3. Introduction of Nga07062 Gene Expression Plasmid into *Escherichia coli*

An *Escherichia coli* mutant strain, strain K27 (fadD88) (Overath et al, Eur. J. Biochem. 7, 559-574, 1969), was transformed by a competent cell transformation method, using each of the Nga07062 gene expression plasmids constructed in the above. Each transformant was cultured overnight at 37° C., and each colony thus obtained was inoculated in 1 mL of LBAmp liquid medium (Bacto Trypton 1%, yeast extract 0.5%, NaCl 1%, and Ampicillin sodium 50 μg/mL), and then cultured overnight at 37° C. Twenty microliters of the culture fluid was inoculated to 2 mL of Overnight Express Instant TB medium (Novagen, Inc.) and was subjected to shaking culture at 30° C. After 16 hours cultivation, lipid components contained in the culture fluid were analyzed by the method described below in the following item 5. As a negative control, *Escherichia coli* strain K27 transformed with the plasmid vector pBluescriptII SK(-) was also subjected to the same experiment.

4. Extraction of Lipid from *Escherichia coli* Culture Fluid and Analysis of Fatty Acid Contained Therein To 1 mL of the culture fluid, 50 μL of 7-pentadecanone (1 mg/mL) as an internal standard was added, and then 0.5 mL of chloroform, 1 mL of methanol and 10 μL of 2N hydrochloric acid were added. The mixture was sufficiently stirred and then was left for 30 minutes. Further, 0.5 mL of chloroform and 0.5 mL of a 1.5% aqueous solution of potassium chloride were added thereto. The mixture was stirred and centrifuged for 15 minutes at 3,000 rpm, and then the chloroform layer (lower layer) was collected with pasteur pipette. A nitrogen gas was blown onto the resultant chloroform layer to be dried into solid, 0.7 mL of 0.5 N potassium hydroxide/methanol solution was added thereto, and the resultant mixture was kept warm at 80° C. for 30 minutes. One milliliter of 14% solution of boron trifluoride (manufactured by Sigma-Aldrich) was added to the sample, and the mixture was kept warm at 80° C. for 10 minutes. Thereafter, 1 mL of saturated saline and 1 mL of hexane were added thereto, and the mixture was sufficiently stirred and then was left for 30 minutes at room temperature. Then, the hexane layer (upper layer) was collected to obtain fatty acid esters.

The obtain fatty acid esters were provided for gas chromatographic analysis. The gas chromatography was carried out under the conditions as follows:

capillary column: DB-1 MS 30 m×200 μm×0.25 μm (J&W Scientific, Inc.),
mobile layer: high purity helium,
flow rate inside the column: 1.0 mL/min,
temperature rise program: 100° C. (for 1 min)→10° C./min→300° C. (for 5 min),
equilibration time: for 1 min,
injection port: split injection (split ratio: 100:1),
pressure 14.49 psi, 104 mL/min,
amount of injection 1 μL,
cleaning vial: methanol•chloroform, and
detector temperature: 300° C.

Moreover, fatty acid ester was identified by providing the identical sample for a gas chromatography-mass spectrometry analysis under identical conditions.

Amounts of fatty acid methyl esters were quantitatively determined based on the peak areas of the above gas chromatographic analysis. The peak area corresponding to the each fatty acids was compared with that of 7-pentadecanone as the internal standard, and carried out corrections between the samples, and then the amount of the each fatty acids per liter of the culture fluid was calculated. Further, the total amount of the each fatty acids was calculated by summing the amounts of the each fatty acids thus obtained, and ratio (weight percent) of the each fatty acids in the total amount of fatty acids was calculated.

Table 2 shows the results of measuring a ratio of each fatty acid and a total amount of fatty acids. Herein, in Table below, the description of "Cx:y" for the fatty acid composition represents a fatty acid having "x" as the number of carbon atoms, and "y" as the number of double bonds.

TABLE 2

| Introduced plasmid | Total amount of fatty acids (mg/L) | Fatty Acid Composition (%) | | | | | | | | |
|---|---|---|---|---|---|---|---|---|---|---|
| | | C12:1 | C12:0 | C14:1 | C14:0 | C16:1 | C16:0 | C17:0 | C18:1 | C19:0 |
| pBS | 149.6 | 0.0 | 0.0 | 0.0 | 4.5 | 2.9 | 49.3 | 26.9 | 9.1 | 7.3 |
| Nga07062__106 | 155.4 | 0.0 | 0.0 | 1.2 | 5.2 | 8.2 | 44.6 | 20.6 | 16.3 | 3.4 |
| Nga07062__163 | 208.7 | 0.0 | 1.2 | 0.8 | 7.9 | 1.9 | 48.4 | 28.2 | 5.1 | 6.4 |
| Nga07062__193 | 284.1 | 0.9 | 1.3 | 4.1 | 7.4 | 14.5 | 41.4 | 14.8 | 12.9 | 2.8 |
| Nga07062__223 | 377.1 | 2.4 | 2.6 | 9.0 | 12.1 | 14.9 | 35.0 | 12.8 | 8.7 | 2.7 |
| Nga07062__253 | 377.4 | 3.1 | 2.8 | 10.4 | 11.1 | 17.2 | 32.7 | 11.1 | 8.8 | 2.8 |
| Nga07062__283 | 373.0 | 2.6 | 2.6 | 9.0 | 12.3 | 15.3 | 34.7 | 12.5 | 8.1 | 3.0 |
| Nga07062__313 | 303.2 | 1.9 | 2.2 | 7.3 | 11.2 | 12.8 | 37.3 | 15.6 | 8.2 | 3.4 |
| Nga07062__343 | 245.2 | 0.7 | 1.7 | 3.0 | 9.4 | 8.6 | 43.2 | 21.1 | 8.0 | 4.2 |

As shown in Table 2, an increase in a total amount of fatty acids was observed in the transformant having the Nga07062 gene fragment in comparison with the transformant (pBS of Table 2) having the plasmid vector pBluescriptII SK(-). Moreover, the fatty acid composition changed in the transformant in comparison with the transformant having the plasmid vector pBluescriptII SK(-). In particular, ratios of the fatty acids of C12:1, C12:0, C14:1, C14:0 and C16:1 increased. From these results, the protein encoded by the Nga07062 gene is thought to be the acyl-ACP thioesterase in which a specific fatty acid is cut out from acyl-ACP. Moreover, a protein containing at least the amino acid sequence of the 115$^{th}$ to 274$^{th}$ amino acids set forth in SEQ ID NO: 1 was found to show the acyl-ACP thioesterase activity.

Example 2. Preparation of *Escherichia coli* Transformant Having Acyl-ACP Thioesterase Gene Derived from *Nannochloropsis oculata*, and Production of Lipid by *Escherichia coli* Transformant

1. Preparation of Gene Encoding Acyl-ACP Thioesterase Derived from *Nannochloropsis oculata* (Hereinafter, Referred to as "NoTE"), and Construction of Plasmid for NoTE Gene Expression Total RNA of *Nannochloropsis oculata* NIES 2145 was extracted, and reverse transcription was performed using SuperScript (trade name) III First-Strand Synthesis Super-Mix for qRT-PCR (manufactured by Invitrogen Corporation) to obtain cDNA. This cDNA was used as a template, and a gene fragment consisting of a nucleotide sequence set forth in SEQ ID NO: 15 was prepared by PCR using a pair of primers set forth in SEQ ID NO: 18 and SEQ ID NO: 27 shown in Table 3 below. The resultant gene fragment was subjected to cloning to the plasmid vector pBluescriptII SK(−) in a manner similar to the method in the item 2. in Example 1 to construct a plasmid NoTE_1 for NoTE gene expression. This expression plasmid was constructed in the form of fusing on a side of an N-terminus of $1^{st}$ amino acid of an amino acid sequence (SEQ ID NO: 14) encoded by the NoTE gene with the amino acid sequence of the $1^{st}$ to $29^{th}$ amino acids on the side of the N-terminus of the LacZ protein derived from the plasmid.

In a similar manner, the cDNA was used a template, and PCR was carried out by using pairs of any one of primers set forth in SEQ ID NOs: 19 to 26, and a primer set forth in SEQ ID NO: 27, shown in Table 3 below, to prepare a gene fragment consisting of a nucleotide sequence of the $145^{th}$ to $864^{th}$ nucleotides set forth in SEQ ID NO: 15, a gene fragment consisting of a nucleotide sequence of the $172^{nd}$ to $864^{th}$ nucleotides set forth in SEQ ID NO: 15, a gene fragment consisting of a nucleotide sequence of the $232^{nd}$ to $864^{th}$ nucleotides set forth in SEQ ID NO: 15, a gene fragment consisting of a nucleotide sequence of the $262^{nd}$ to $864^{th}$ nucleotides set forth in SEQ ID NO: 15, a gene fragment consisting of a nucleotide sequence of the $292^{nd}$ to $864^{th}$ nucleotides set forth in SEQ ID NO: 15, a gene fragment consisting of a nucleotide sequence of the $322^{nd}$ to $864^{th}$ nucleotides set forth in SEQ ID NO: 15, a gene fragment consisting of a nucleotide sequence the $352^{nd}$ to $864^{th}$ nucleotides set forth in SEQ ID NO: 15, and a gene fragment consisting of a nucleotide sequence the $382^{nd}$ to $864^{th}$ nucleotides set forth in SEQ ID NO: 15, respectively. Each of the resultant gene fragments was fused with the pBluescriptII SK(−) vector in a manner similar to the method described above to construct a plasmid NoTE_145 for NoTE gene expression, a plasmid NoTE_172 therefor, a plasmid NoTE_232 therefor, a plasmid NoTE_262 therefor, a plasmid NoTE_292 therefor, a plasmid NoTE_322 therefor, a plasmid NoTE_352 therefor, and a plasmid NoTE_382 therefor, respectively. Herein, these expression plasmids were constructed in the form of removing amino acid sequences of the $1^{st}$ to $48^{th}$ amino acids, the $1^{st}$ to $57^{th}$ amino acids, the $1^{st}$ to $77^{th}$ amino acids, the $1^{st}$ to $87^{th}$ amino acids, the $1^{st}$ to $97^{th}$ amino acids, the $1^{st}$ to $107^{th}$ amino acids, the $1^{st}$ to $117^{th}$ amino acids or the $1^{st}$ to $127^{th}$ amino acids on the side of the N-terminus of the amino acid sequence (SEQ ID NO: 14) encoded by the NoTE gene, respectively, and fusing with the amino acid sequence of the $1^{st}$ to $29^{th}$ amino acids on the side of the N-terminus of the LacZ protein derived from the plasmid.

TABLE 3

| | Nucleotide Sequence of Primers |
|---|---|
| SEQ ID NO: 18 | GCGGCCGCTCTAGAGATGACGCCTTTGGCCTTCAC |
| SEQ ID NO: 19 | GCGGCCGCTCTAGAGTCCGGCTGTTCACATAGCAC |
| SEQ ID NO: 20 | GCGGCCGCTCTAGAGCTTAGAACCAGCTTCCCAGTC |
| SEQ ID NO: 21 | GCGGCCGCTCTAGAGGCTGCCATTTCCCTGCCGTCG |
| SEQ ID NO: 22 | GCGGCCGCTCTAGAGTGCGAGACGGCCCACGCCGGGAC |
| SEQ ID NO: 23 | GCGGCCGCTCTAGAGAGACGAGGTGAGAGGAAGGC |
| SEQ ID NO: 24 | GCGGCCGCTCTAGAGGATGGTGGAAAAGGCGAGGCC |
| SEQ ID NO: 25 | GCGGCCGCTCTAGAGGCTACATGCAATCCATCCTTATTC |
| SEQ ID NO: 26 | GCGGCCGCTCTAGAGCATGATCGCGTCGACACCAAGC |
| SEQ ID NO: 27 | ACAAAATATTAACGCCTAGCTAATATCAATTTTCTTTGG |

2. Introduction of NoTE Gene Expression Plasmid into *Escherichia coli*, Extraction of Lipid from *Escherichia coli* Culture Fluid, and Analysis of Fatty Acid Contained Therein The NoTE expression plasmid was introduced into *Escherichia coli* in a manner similar to the method in item 3. in Example 1 to analyze a lipid in a manner similar to the method in item 4. in Example 1.

TABLE 4

| Introduced plasmid | Total amount of fatty acids (mg/L) | Fatty Acid Composition (%) | | | | | | | | |
|---|---|---|---|---|---|---|---|---|---|---|
| | | C12:1 | C12:0 | C14:1 | C14:0 | C16:1 | C16:0 | C17:0 | C18:1 | C19:0 |
| pBS | 228.0 | 0.0 | 0.0 | 0.0 | 4.7 | 3.5 | 47.3 | 27.9 | 11.4 | 5.2 |
| NoTE_1 | 348.8 | 1.3 | 2.2 | 6.9 | 10.2 | 11.8 | 35.9 | 16.9 | 11.9 | 2.9 |
| NoTE_145 | 372.4 | 2.1 | 2.6 | 10.0 | 10.4 | 18.1 | 32.4 | 11.4 | 11.6 | 1.4 |
| NoTE_172 | 364.7 | 1.1 | 1.4 | 5.4 | 5.5 | 23.1 | 37.6 | 10.1 | 15.1 | 0.6 |
| NoTE_232 | 429.2 | 4.5 | 3.0 | 15.9 | 12.4 | 24.8 | 23.8 | 8.4 | 6.6 | 0.7 |
| NoTE_262 | 360.6 | 6.5 | 3.9 | 18.8 | 13.6 | 25.9 | 19.2 | 7.0 | 4.8 | 0.4 |
| NoTE_292 | 460.2 | 2.8 | 2.3 | 12.0 | 10.8 | 21.7 | 28.9 | 10.6 | 9.1 | 1.8 |
| NoTE_322 | 441.5 | 4.5 | 3.0 | 16.0 | 11.9 | 24.5 | 23.4 | 9.0 | 6.7 | 1.0 |
| NoTE_352 | 299.2 | 3.7 | 2.2 | 10.2 | 7.2 | 26.3 | 30.9 | 9.1 | 9.8 | 0.7 |
| NoTE_382 | 349.3 | 1.5 | 1.6 | 5.9 | 5.7 | 21.2 | 37.5 | 11.2 | 14.6 | 0.8 |

As shown in Table 4, an increase in a total amount of fatty acids was observed in the transformant having the NoTE gene fragment in comparison with the transformant (pBS of Table 4) having the plasmid vector pBluescriptII SK(−). Moreover, the fatty acid composition changed in the transformant in comparison with the transformant having the plasmid vector pBluescriptII SK(−). In particular, ratios of the fatty acids of C12:1, C12:0, C14:1, C14:0 and C16:1 increased. From these results, the protein encoded by the NoTE gene is thought to be the acyl-ACP thioesterase in which a specific fatty acid is cut out from acyl-ACP. Moreover, a protein containing at least the amino acid sequence of the $128^{th}$ to $287^{th}$ amino acids set forth in SEQ ID NO: 14 was found to show the acyl-ACP thioesterase activity.

Example 3. Preparation of *Escherichia coli* Transformant Having Acyl-ACP Thioesterase Gene Derived from *Nannochloropsis granulata*, and Production of Lipid by *Escherichia coli* Transformant 1. Preparation of Gene Encoding Acyl-ACP Thioesterase Derived from *Nannochloropsis granulata* (Hereinafter, Referred to as "NgrTE"), and Construction of Plasmid for NgrTE Gene Expression Total RNA of *Nannochloropsis granulata* NIES2588 was extracted, and reverse transcription was performed using SuperScript (trade name) III First-Strand Synthesis Super-Mix for qRT-PCR (manufactured by Invitrogen Corporation) to obtain cDNA. This cDNA was used as a template, and a gene fragment consisting of a nucleotide sequence set forth in SEQ ID NO: 17 was prepared by PCR using a pair of primers set forth in SEQ ID NO: 28 and SEQ ID NO: 33 shown in Table 5 below. The resultant gene fragment was subjected to cloning to the plasmid vector pBluescriptII SK(−) in a manner similar to the method in the item 2. in Example 1 to construct a plasmid NgrTE_1 for NgrTE gene expression. This expression plasmid was constructed in the form of fusing on a side of an N-terminus of $1^{st}$ amino acid of an amino acid sequence (SEQ ID NO: 16) encoded by the NgrTE gene with the amino acid sequence of the $1^{st}$ to $29^{th}$ amino acids on the side of the N-terminus of the LacZ protein derived from the plasmid.

In a similar manner, the cDNA was used a template, and PCR was carried out by using pairs of any one of primers set forth in SEQ ID NOs: 29 to 32, and a primer set forth in SEQ ID NO: 33 shown in Table 5 below, to prepare a gene fragment consisting of a nucleotide sequence of the $103^{rd}$ to $858^{th}$ nucleotides set forth in SEQ ID NO: 17, a gene fragment consisting of a nucleotide sequence of the $183^{rd}$ to $858^{th}$ nucleotides set forth in SEQ ID NO: 17, a gene fragment consisting of a nucleotide sequence of the $253^{rd}$ to $858^{th}$ nucleotides set forth in SEQ ID NO: 17, and a gene fragment consisting of a nucleotide sequence of the $376^{th}$ to $858^{th}$ nucleotides set forth in SEQ ID NO: 17, respectively. Each of the resultant gene fragments was fused with the pBluescriptII SK(−) vector in a manner similar to the method described above to construct a plasmid NgrTE_103 for NgrTE gene expression, a plasmid NgrTE_163 therefor, a plasmid NgrTE_253 therefor, and a plasmid NgrTE_376 therefor, respectively. Herein, these expression plasmids were constructed in the form of removing amino acid sequences of the $1^{st}$ to $34^{th}$ amino acids, the $1^{st}$ to $54^{th}$ amino acids, the $1^{st}$ to $84^{th}$ amino acids or the $1^{st}$ to $125^{th}$ amino acids on the side of the N-terminus of the amino acid sequence (SEQ ID NO: 16) encoded by the NgrTE gene, respectively, and fusing with the amino acid sequence of the $1^{st}$ to $29^{th}$ amino acids on the side of the N-terminus of the LacZ protein derived from the plasmid.

TABLE 5

| | Nucleotide Sequence of Primers |
|---|---|
| SEQ ID NO: 28 | GCGGCCGCTCTAGAGATGACGCCTTTGGCCTTCAC |
| SEQ ID NO: 29 | GCGGCCGCTCTAGAGTCCTCCCAGGTCACTCGACC |
| SEQ ID NO: 30 | GCGGCCGCTCTAGAGACACTTAGCAACAGCTTTCC |
| SEQ ID NO: 31 | GCGGCCGCTCTAGAGCTATGTGAGACGGCCCACAC |
| SEQ ID NO: 32 | GCGGCCGCTCTAGAGCATGATCGCGTCGACACGAAG |
| SEQ ID NO: 33 | ACAAAATATTAACGCCTAGCTAATGTCAATTTTCTTTGG |

2. Introduction of NgrTE Gene Expression Plasmid into *Escherichia coli*, Extraction of Lipid from *Escherichia coli* Culture Fluid, and Analysis of Fatty Acid Contained Therein The NgrTE expression plasmid was introduced into *Escherichia coli* in a manner similar to the method in item 3. in Example 1 to analyze a lipid in a manner similar to the method in item 4. in Example 1.

TABLE 6

| Introduced plasmid | Total amount of fatty acids (mg/L) | Fatty Acid Composition (%) | | | | | | | | |
|---|---|---|---|---|---|---|---|---|---|---|
| | | C12:1 | C12:0 | C14:1 | C14:0 | C16:1 | C16:0 | C17:0 | C18:1 | C19:0 |
| pBS | 181.4 | 0.0 | 0.0 | 0.0 | 6.4 | 2.5 | 48.1 | 28.3 | 5.9 | 8.7 |
| NgrTE_1 | 317.1 | 2.1 | 3.9 | 9.1 | 14.9 | 10.1 | 33.5 | 14.2 | 6.9 | 5.1 |
| NgrTE_103 | 344.0 | 2.8 | 4.0 | 12.3 | 14.1 | 14.5 | 29.7 | 11.2 | 7.9 | 3.3 |
| NgrTE_163 | 328.4 | 2.2 | 4.1 | 9.4 | 14.9 | 9.9 | 32.9 | 14.6 | 7.0 | 4.9 |
| NgrTE_253 | 414.1 | 4.5 | 4.1 | 16.5 | 12.6 | 19.3 | 24.3 | 8.9 | 7.3 | 2.6 |
| NgrTE_376 | 296.4 | 1.4 | 2.1 | 6.6 | 9.9 | 9.9 | 36.5 | 17.7 | 8.1 | 7.9 |

As shown in Table 6, an increase in a total amount of fatty acids was observed in the transformant having the NgrTE gene fragment in comparison with the transformant (pBS of Table 6) having the plasmid vector pBluescriptII SK(−). Moreover, the fatty acid composition changed in the transformant in comparison with the transformant having the plasmid vector pBluescriptII SK(−). In particular, ratios of the fatty acids of C12:1, C12:0, C14:1, C14:0 and C16:1 increased.

Example 4. Preparation of *Escherichia coli* Transformant Having Mutated NoTE Gene, and Production of Lipid by *Escherichia coli* Transformant 1. Preparation of Mutated NoTE Gene, and Construction of Plasmid for Mutated NoTE Gene Expression A gene sequence (SEQ ID NO: 35) encoding a mutated NoTE set forth in SEQ ID NO: 34 was prepared using custom synthesis service of an artificial gene. The amino acid sequence of the 128th to 287th amino acids set forth in SEQ ID NO: 34 shows about 84% identity with the amino acid sequence of the 115th to 274th amino acids set forth in SEQ ID NO: 1.

This gene fragment was used as a template, and a gene fragment consisting of a nucleotide sequence set forth in SEQ ID NO: 35 was prepared by PCR using a pair of primers set forth in SEQ ID NO: 22 shown in Table 3 above and SEQ ID NO: 36 and shown in Table 7 below. The resultant gene fragment was subjected to cloning to a plasmid vector pBluescriptII SK(−) in a manner similar to the method in item 2. in Example 1 to construct a plasmid NoTE_262-mutant for mutated NoTE gene expression. This expression plasmid was constructed in the form of removing an amino acid sequence of the 1st to 87th amino acids on a side of an N-terminus of an amino acid sequence (SEQ ID NO: 34) encoded by a mutated NoTE gene, and further fusing with the amino acid sequence of the 1st to 29th amino acids on the side of the N-terminus of the LacZ protein derived from the plasmid.

TABLE 7

| | Nucleotide Sequence of Primer |
|---|---|
| SEQ ID NO: 36 | ACAAAATATTAACGCCTAGCTAGTAGCAATTTTCC |

2. Introduction of Mutated NoTE Gene Expression Plasmid into *Escherichia coli*, Extraction of Lipid from *Escherichia coli* Culture Fluid, and Analysis of Fatty Acid Contained Therein The mutated-NoTE expression plasmid was introduced into *Escherichia coli* in a manner similar to the method in item 3. in Example 1 to analyze a lipid in a manner similar to the method in item 4. in Example 1.

A VCP1 promoter sequence (SEQ ID NO: 54), a VCP chloroplast transit peptide sequence (SEQ ID NO: 55) and a VCP1 terminator sequence (SEQ ID NO: 56) were artificially synthesized based on the complete cds sequence (Accession number: JF957601.1) of the VCP1 (violaxanthin/(chlorophyll a)-binding protein) gene of *Nannochloropsis* sp. W2J3B registered in GenBank. The thus-synthesized DNA fragment was used as a template, and PCR was carried out using a pair of primers set forth in SEQ ID NO: 39 and SEQ ID NO: 40, a pair of primers set forth in SEQ ID NO: 41 and SEQ ID NO: 42, and a pair of primers set forth in SEQ ID NO: 43, and SEQ ID NO: 44 as shown in Table 9 below to prepare the VCP1 promoter sequence, the VCP1 chloroplast transit peptide sequence and the VCP1 terminator sequence, respectively. Moreover, a plasmid vector pUC19 (manufactured by TAKARA BIO Inc.) was used as a template, and PCR using a pair of primers set forth in SEQ ID NO: 45 and SEQ ID NO: 46 shown in Table 9 below was carried out to amplify the plasmid vector pUC19.

The NoTE gene fragment, the VCP1 promoter sequence, the VCP1 chloroplast transit peptide sequence and the VCP1 terminator sequence obtained as described above were fused with the plasmid vector pUC19 in a manner similar to the method in item 2. in Example 1 to construct an expression plasmid NoTE_292_Nanno in *Nannochloropsis*. This expression plasmid consisted of the pUC19 vector sequence and an insert sequence (SEQ ID NO: 57; hereinafter, referred to as "fragment for NoTE gene expression") in which the VCP1 promoter sequence, the VCP1 chloroplast transit peptide sequence, the NoTE gene fragment and the VCP1 terminator sequence were linked in this order.

2. Construction of Plasmid for Zeocin Resistance Gene Expression in *Nannochloropsis*

A Zeocin resistance gene (SEQ ID NO: 58), and a tubulin promoter sequence (SEQ ID NO: 59) derived from *Nanno-*

TABLE 8

| Introduced plasmid | Total amount of fatty acids (mg/L) | Fatty Acid Composition (%) | | | | | | | | |
|---|---|---|---|---|---|---|---|---|---|---|
| | | C12:1 | C12:0 | C14:1 | C14:0 | C16:1 | C16:0 | C17:0 | C18:1 | C19:0 |
| pBS | 203.8 | 0.0 | 0.0 | 0.0 | 5.3 | 1.6 | 46.3 | 29.2 | 4.3 | 13.2 |
| NoTE_262-mutant | 511.9 | 5.5 | 5.5 | 7.7 | 19.7 | 13.5 | 27.9 | 9.4 | 6.3 | 4.5 |

As shown in Table 8, an increase in a total amount of fatty acids was observed in the transformant having the mutated-NoTE gene fragment in comparison with the transformant (pBS of Table 8) having the plasmid vector pBluescriptII SK(−). Moreover, the fatty acid composition changed in the transformant in comparison with the transformant having the plasmid vector pBluescriptII SK(−). In particular, ratios of the fatty acids of C12:1, C12:0, C14:1, C14:0 and C16:1 increased. From these results, the mutated-NoTE was found to show the acyl-ACP thioesterase activity.

Example 5. Preparation of *Nannochloropsis* Transformant Having NoTE Gene, and Production of Lipid by *Nannochloropsis* Transformant 1. Construction of Plasmid for NoTE Gene Expression The cDNA of *Nannochloropsis oculata* NIES 2145 was used as a template, and PCR using a pair of primers set forth in SEQ ID NO: 37 and SEQ ID NO: 38 shown in Table 9 below was carried out to prepare a NoTE gene fragment consisting of a nucleotide sequence of the 292nd to 864th nucleotides set forth in SEQ ID NO: 15.

*chloropsis gaditana* CCMP 526 described in literature (Randor Radakovits, et al., Nature Communications, DOI: 10.1038/ncomms1688, 2012) were artificially synthesized. The thus-synthesized DNA fragment was used as a template, and PCR was carried out using a pair of primers set forth in SEQ ID NO: 47 and SEQ ID NO: 48, and a pair of primers set forth in SEQ ID NO: 49 and SEQ ID NO: 50, to prepare a Zeocin resistance gene and a tubulin promoter sequence, respectively. These amplified fragments were fused with the VCP1 terminator sequence and the amplified fragment of a plasmid vector pUC19 prepared in item 1. as described above in a manner similar to the method in item 2. in Example 1 to construct a Zeocin resistance gene expression plasmid. This expression plasmid consisted of a pUC19 vector sequence, and an insert sequence (SEQ ID NO: 60; hereinafter, referred to as "fragment for Zeocin resistance gene expression") in which the tubulin promoter sequence, the Zeocin resistance gene, and the VCP1 terminator sequence were linked in this order.

3. Introduction of Fragment for NoTE Gene Expression into *Nannochloropsis*

The expression plasmid NoTE_292_Nanno was used as a template, and PCR was carried out using a pair of primers set forth in SEQ ID NO: 51 and SEQ ID NO: 52 shown in Table 9 below to amplify a fragment for NoTE gene expression (SEQ ID NO: 57) in the plasmid. Moreover, the plasmid for Zeocin resistance gene expression was used as a template, and PCR was carried out using a pair of primers set forth in SEQ ID NO: 52 and SEQ ID NO: 53 to amplify a fragment for Zeocin resistance gene expression (SEQ ID NO: 60). Both of amplified fragments were purified using a High Pure PCR Product Purification Kit (manufactured by Roche Applied Science Corporation). Herein, sterilized water was used for elution upon purification without using an elution buffer included in the kit.

About $10^9$ cells of *Nannochloropsis oculata* NIES 2145 were washed with a 384 mM sorbitol solution to completely remove a salt, and the resultant was used as a host cell of transformation. The amplified fragment for NoTE gene expression (SEQ ID NO: 57) and fragment for Zeocin resistance gene expression (SEQ ID NO: 60) as described above were mixed by about 500 ng for each with the host cell, and electroporation was carried out under conditions of 50 μF, 500Ω and 2,200 v/2 mm. After 24 hours cultivation in an f/2 liquid medium, the resultant material was inoculated in an f/2 agar medium containing 2 μg/mL of Zeocin, and cultured for two to three weeks under 12 h/12 h light-dark conditions at 25° C. under an atmosphere of 0.3% $CO_2$. A transformant containing the fragment for NoTE gene expression (SEQ ID NO: 57) was selected from the resultant colonies by a PCR method. The thus-selected strain was seeded to 20 mL of a culture medium (hereinafter, referred to as "N15P5 medium") in which a nitrogen concentration in the f/2 medium was reinforced 15 times, and a phosphorus concentration therein was reinforced 5 times, and subjected to shaking culture for four weeks under the 12 h/12 h light-dark conditions at 25° C. under the atmosphere of 0.3% $CO_2$ (preculture). Then, 2 mL of the preculture fluid was subcultured to 18 mL of the N15P5 medium, and subjected to shaking culture for two weeks under the 12 h/12 h light-dark conditions at 25° C. under the atmosphere of 0.3% $CO_2$. In addition, as a negative control, an experiment was also conducted on NIES 2145 being wild-type.

TABLE 9

| | Nucleotide Sequence of Primers |
|---|---|
| SEQ ID NO: 37 | CGCGGTGTTGCGCGCAGACGAGGTGAGAGGAAGGC |
| SEQ ID NO: 38 | CTCTTCCACAGAAGCCTAGCTAATATCAATTTTCTTTGG |
| SEQ ID NO: 39 | CGAGCTCGGTACCCGGGCGGTCTTTTGTCCTTTCCTC |
| SEQ ID NO: 40 | AATCTGCTCGGAGGGGAGGATC |
| SEQ ID NO: 41 | CCCTCCGAGCAGATTATGAAGACCGCCGCTCTCCTC |
| SEQ ID NO: 42 | GCGCGCAACACCGCGGGTGCGGGAGAAC |
| SEQ ID NO: 43 | GCTTCTGTGGAAGAGCCAGTG |
| SEQ ID NO: 44 | ACTCTAGAGGATCCCCTGATCTTGTCCATCTCGTG |
| SEQ ID NO: 45 | GGGATCCTCTAGAGTCGACC |
| SEQ ID NO: 46 | CGGGTACCGAGCTCGAATTC |
| SEQ ID NO: 47 | CTTTTTTGTGAAGCAATGGCCAAGTTGACCAGTGCCG |
| SEQ ID NO: 48 | CTCTTCCACAGAAGCTTAGTCCTGCTCCTCGGCCACG |
| SEQ ID NO: 49 | CGAGCTCGGTACCCGACTGCGCATGGATTGACCGA |
| SEQ ID NO: 50 | TGCTTCACAAAAAAGACAGCTTCTTGAT |
| SEQ ID NO: 51 | GGCGGTCTTTTGTCCTTTCCTC |
| SEQ ID NO: 52 | CTGATCTTGTCCATCTCGTG |
| SEQ ID NO: 53 | ACTGCGCATGGATTGACCGA |

2. Extraction of Lipid from *Nannochloropsis* Culture Fluid, and Analysis of Fatty Acid Contained Therein After the culture, lipid of the resultant *Nannochloropsis* culture fluid was extracted and analyzed in a manner similar to the method in item 4. in Example 1. Table 10 shows the results. In addition, in Table 10, "n" represents an integer of 0 to 5. For example, when "C18:n" was described, the description represents a total of fatty acids having compositions of C18:0, C18:1, C18:2, C18:3, C18:4 and C18:5.

TABLE 10

| | Total amount of fatty acids (mg/L) | Fatty Acid Composition (%) | | | | | |
|---|---|---|---|---|---|---|---|
| | | C12:0 | C14:0 | C16:1 | C16:0 | C18:n | C20:n |
| Wild type | 1108 ± 169 | 0.1 ± 0.0 | 3.9 ± 0.2 | 28.9 ± 1.0 | 35.5 ± 1.4 | 19.0 ± 0.3 | 12.7 ± 2.1 |
| NoTE-Introduced strain | 1352 ± 59 | 0.3 ± 0.0 | 6.3 ± 0.1 | 30.6 ± 0.3 | 36.1 ± 0.3 | 16.3 ± 0.2 | 10.4 ± 0.4 |

As shown in Table 10, in the *Nannochloropsis* transformant ("NoTE-introduced strain" in Table 10) having the NoTE gene fragment, an increase in a total amount of fatty acid was observed in comparison with the *Nannochloropsis* NIES2145 ("wild-type" in Table 10) being the host. Moreover, in the transformant, ratios of fatty acids of C12:0 and C14:0 significantly increased in comparison with the *Nannochloropsis* NIES2145 (p<0.01 for all).

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2012-286058 filed in Japan on Dec. 27, 2012, which is entirely herein incorporated by reference.

What is claimed is:

1. A method of modifying a fatty acid composition in a lipid, comprising introducing a gene encoding a protein selected from the following (a) to (c) or a recombinant vector comprising the gene into a host:

(a) A protein consisting of the amino acid sequence of the 115th to 274th amino acids set forth in SEQ ID NO: 1;

(b) A protein consisting of an amino acid sequence having 90% or more identity with the amino acid sequence of the protein (a), and having acyl-ACP thioesterase activity; and (c) A protein comprising an amino acid sequence selected from (i) to (x) below, but not the amino acid sequence of SEQ ID NO:1, and having acyl-ACP thioesterase activity:

(i) the amino acid sequence of the 36th to 274th amino acids set forth in SEQ ID NO: 1;

(ii) the amino acid sequence of the 45th to 274th amino acids set forth in SEQ ID NO: 1;

ii) the amino acid sequence of the 55th to 274th amino acids set forth in SEQ ID NO: 1;

(iv) the amino acid sequence of the 65th to 274th amino acids set forth in SEQ ID NO: 1;

(v) the amino acid sequence of the 75th to 274th amino acids set forth in SEQ ID NO: 1;

(vi) the amino acid sequence of the 85th to 274th amino acids set forth in SEQ ID NO: 1;

(vii) the amino acid sequence of the 95th to 274th amino acids set forth in SEQ ID NO: 1;

(viii) the amino acid sequence of the 105th to 274th amino acids set forth in SEQ ID NO: 1;

(ix) the amino acid sequence of the $115^{th}$ to $274^{th}$ amino acids set forth in SEQ ID NO: 1; and (x) one of the amino acid sequences of (i)-(ix) but in which 1 or more and 20 or less amino acids are mutated;

expressing the protein in the host cell; and modifying the fatty acid composition of the lipid produced by the host cell as a result of expression of the protein.

2. The method according to claim 1, wherein the protein is protein (b) in which 1 or more and 10 or less amino acids in the sequence of protein (a) are mutated, in which the amino acid sequence of the protein with the mutated amino acid sequence has 90% or more identity with the amino acid sequence of protein (a), and in which the protein with the mutated amino acid sequence has acyl-ACP thioesterase activity.

3. The method according to claim 1, wherein the protein is protein (c) and protein (c) is a protein selected from the group consisting of:

a protein consisting of the amino acid sequence of the 36th to 274th amino acids set forth in SEQ ID NO: 1;

a protein consisting of the amino acid sequence of the 45th to 274th amino acids set forth in SEQ ID NO: 1;

a protein consisting of the amino acid sequence of the 55th to 274th amino acids set forth in SEQ ID NO: 1;

a protein consisting of the amino acid sequence of the 65th to 274th amino acids set forth in SEQ ID NO: 1;

a protein consisting of the amino acid sequence of the 75th to 274th amino acids set forth in SEQ ID NO: 1;
a protein consisting of the amino acid sequence of the 85th to 274th amino acids set forth in SEQ ID NO: 1;
a protein consisting of the amino acid sequence of the 95th to 274th amino acids set forth in SEQ ID NO: 1;
a protein consisting of the amino acid sequence of the 105th to 274th amino acids set forth in SEQ ID NO: 1; and
a protein having any one of these amino acid sequences, in which 1 or more and 20 or less amino acids are mutated, and having acyl-ACP thioesterase activity.

4. The method according to claim 1, wherein the host is a microalga.

5. A method of modifying a fatty acid composition in a lipid, comprising
introducing a gene consisting of any one of the following DNAs (d) to (f) or a recombinant vector comprising the gene into a host:
(d) A DNA consisting of the nucleotide sequence of the 343rd to 825th nucleotides set forth in SEQ ID NO: 2;
(e) A DNA consisting of a nucleotide sequence having 90% or more identity with the nucleotide sequence of the DNA (d), and encoding a protein having acyl-ACP thioesterase activity; and
(f) A DNA comprising a nucleotide sequence selected from (xi) to (xx) below, but not the DNA sequence of SEQ ID NO:2, and encoding a protein having acyl-ACP thioesterase activity:
 (xi) a DNA comprising the nucleotide sequence of the 106th to 825th nucleotides set forth in SEQ ID NO: 2;
 (xii) a DNA comprising the nucleotide sequence of the 133rd to 825th nucleotides set forth in SEQ ID NO: 2;
 (xiii) a DNA comprising the nucleotide sequence of the 163rd to 825th nucleotides set forth in SEQ ID NO: 2;
 (xiv) a DNA comprising the nucleotide sequence of the 193rd to 825th nucleotides set forth in SEQ ID NO: 2;
 (xv) a DNA comprising the nucleotide sequence of the 223rd to 825th nucleotides set forth in SEQ ID NO: 2;
 (xvi) a DNA comprising the nucleotide sequence of the 253rd to 825th nucleotides set forth in SEQ ID NO: 2;
 (xvii) a DNA comprising the nucleotide sequence of the 283rd to 825th nucleotides set forth in SEQ ID NO: 2;
 (xviii) a DNA comprising the nucleotide sequence of the 313rd to 825th nucleotides set forth in SEQ ID NO: 2;
 (xix) a DNA comprising the nucleotide sequence of the $343^{rd}$ to $825^{th}$ nucleotides set forth in SEQ ID NO: 2; and
 (xx) a DNA comprising any one of nucleotide sequences (xi)-(xix), in which 1 or more and 20 or less nucleotides are mutated, and encoding a protein having acyl-ACP thioesterase activity;
expressing the DNA in the host cell; and
modifying the fatty acid composition of the lipid produced by the host cell as a result of expression of the DNA.

6. The method according to claim 5, wherein the DNA is DNA (e) in which 1 or more and 10 or less nucleotides in the sequence of DNA (d) are mutated, in which the DNA sequence of the DNA with the mutated nucleotide sequence has 90% or more identity with the nucleotide sequence of DNA (d), and in which the DNA with the mutated nucleotide sequence encodes a protein having acyl-ACP thioesterase activity.

7. The method according to claim 5, wherein the DNA is DNA (f) and DNA (f) is a DNA selected from the group consisting of:
a DNA consisting of the nucleotide sequence of the 106th to 825th nucleotides set forth in SEQ ID NO: 2;
a DNA consisting of the nucleotide sequence of the 133rd to 825th nucleotides set forth in SEQ ID NO: 2;
a DNA consisting of the nucleotide sequence of the 163rd to 825th nucleotides set forth in SEQ ID NO: 2;
a DNA consisting of the nucleotide sequence of the 193rd to 825th nucleotides set forth in SEQ ID NO: 2;
a DNA consisting of the nucleotide sequence of the 223rd to 825th nucleotides set forth in SEQ ID NO: 2;
a DNA consisting of the nucleotide sequence of the 253rd to 825th nucleotides set forth in SEQ ID NO: 2;
a DNA consisting of the nucleotide sequence of the 283rd to 825th nucleotides set forth in SEQ ID NO: 2;
a DNA consisting of the nucleotide sequence of the 313rd to 825th nucleotides set forth in SEQ ID NO: 2; and
a DNA having any one of these nucleotide sequences, in which 1 or more and 20 or less nucleotides are mutated, and encoding a protein having acyl-ACP thioesterase activity.

8. The method according to claim 5, wherein the host is a microalga.

9. A method of enhancing productivity of a lipid, comprising
introducing a gene encoding a protein selected from the following (a) to (c) or a recombinant vector comprising the gene into a host:
(a) A protein consisting of the amino acid sequence of the 115th to 274th amino acids set forth in SEQ ID NO: 1;
(b) A protein consisting of an amino acid sequence having 90% or more identity with the amino acid sequence of the protein (a), and having acyl-ACP thioesterase activity; and
(c) A protein comprising an amino acid sequence selected from (i) to (x) below, but not the amino acid sequence of SEQ ID NO:1, and having acyl-ACP thioesterase activity:
 (i) the amino acid sequence of the 36th to 274th amino acids set forth in SEQ ID NO: 1;
 (ii) the amino acid sequence of the 45th to 274th amino acids set forth in SEQ ID NO: 1;
 (iii) the amino acid sequence of the 55th to 274th amino acids set forth in SEQ ID NO: 1;
 the amino acid sequence of the 65th to 274th amino acids set forth in SEQ ID NO: 1;
 (v) the amino acid sequence of the 75th to 274th amino acids set forth in SEQ ID NO: 1;
 (vi) the amino acid sequence of the 85th to 274th amino acids set forth in SEQ ID NO: 1;
 (vii) the amino acid sequence of the 95th to 274th amino acids set forth in SEQ ID NO: 1;
 (viii) the amino acid sequence of the 105th to 274th amino acids set forth in SEQ ID NO: 1;
 (ix) the amino acid sequence of the $115^{th}$ to $274^{th}$ amino acids set forth in SEQ ID NO: 1; and
 (x) one of the amino acid sequences of (i)-(ix) but in which 1 or more and 20 or less amino acids are mutated;

expressing the protein in the host cell; and enhancing productivity of the lipid produced by the host cell as a result of expression of the protein.

10. The method according to claim 9, wherein the protein is protein (b) in which 1 or more and 10 or less amino acids in the sequence of protein (a) are mutated, in which the amino acid sequence of the protein with the mutated amino acid sequence has 90% or more identity with the amino acid sequence of protein (a), and in which the protein with the mutated amino acid sequence has acyl-ACP thioesterase activity.

11. The method according to claim 9, wherein the protein is protein (c) and protein (c) is a protein selected from the group consisting of:

a protein consisting of the amino acid sequence of the 36th to 274th amino acids set forth in SEQ ID NO: 1;
a protein consisting of the amino acid sequence of the 45th to 274th amino acids set forth in SEQ ID NO: 1;
a protein consisting of the amino acid sequence of the 55th to 274th amino acids set forth in SEQ ID NO: 1;
a protein consisting of the amino acid sequence of the 65th to 274th amino acids set forth in SEQ ID NO: 1;
a protein consisting of the amino acid sequence of the 75th to 274th amino acids set forth in SEQ ID NO: 1;
a protein consisting of the amino acid sequence of the 85th to 274th amino acids set forth in SEQ ID NO: 1;
a protein consisting of the amino acid sequence of the 95th to 274th amino acids set forth in SEQ ID NO: 1;
a protein consisting of the amino acid sequence of the 105th to 274th amino acids set forth in SEQ ID NO: 1; and
a protein having any one of these amino acid sequences, in which 1 or more and 20 or less amino acids are mutated, and having acyl-ACP thioesterase activity.

12. The method according to claim 9, wherein the host is a microalga.

13. A method of enhancing productivity of a lipid, comprising introducing a gene consisting of any one of the following DNAs (d) to (f) or a recombinant vector comprising the gene into a host:

(d) A DNA consisting of the nucleotide sequence of the 343rd to 825th nucleotides set forth in SEQ ID NO: 2;
(e) A DNA consisting of a nucleotide sequence having 90% or more identity with the nucleotide sequence of the DNA (d), and encoding a protein having acyl-ACP thioesterase activity; and
(f) A DNA comprising a nucleotide sequence selected from (xi) to (xx) below, but not the DNA sequence of SEQ ID NO:2, and encoding a protein having acyl-ACP thioesterase activity:

(xi) a DNA comprising the nucleotide sequence of the 106th to 825th nucleotides set forth in SEQ ID NO: 2;
(xii) a DNA comprising the nucleotide sequence of the 133rd to 825th nucleotides set forth in SEQ ID NO: 2;
(xiii) a DNA comprising the nucleotide sequence of the 163rd to 825th nucleotides set forth in SEQ ID NO: 2;
(xiv) a DNA comprising the nucleotide sequence of the 193rd to 825th nucleotides set forth in SEQ ID NO: 2;
(xv) a DNA comprising the nucleotide sequence of the 223rd to 825th nucleotides set forth in SEQ ID NO: 2;
(xvi) a DNA comprising the nucleotide sequence of the 253rd to 825th nucleotides set forth in SEQ ID NO: 2;
(xvii) a DNA comprising the nucleotide sequence of the 283rd to 825th nucleotides set forth in SEQ ID NO: 2;
(xviii) a DNA comprising the nucleotide sequence of the 313rd to 825th nucleotides set forth in SEQ ID NO: 2;
(xix) a DNA comprising the nucleotide sequence of the $343^{rd}$ to $825^{th}$ nucleotides set forth in SEQ ID NO: 2; and
(xx) a DNA comprising any one of nucleotide sequences (xi)-(xix), in which 1 or more and 20 or less nucleotides are mutated, and encoding a protein having acyl-ACP thioesterase activity;

expressing the DNA in the host cell; and
modifying the fatty acid composition of the lipid produced by the host cell as a result of expression of the DNA.

14. The method according to claim 13, wherein the DNA is DNA (e) in which 1 or more and 10 or less nucleotides are mutated, in which the DNA sequence of the DNA with the mutated nucleotide sequence has 90% or more identity with the nucleotide sequence of DNA (d), and in which the DNA with the mutated nucleotide sequence encodes a protein having acyl-ACP thioesterase activity.

15. The method according to claim 13, wherein the DNA is DNA (f) and DNA (f) is a DNA selected from the group consisting of:

a DNA consisting of the nucleotide sequence of the 106th to 825th nucleotides set forth in SEQ ID NO: 2;
a DNA consisting of the nucleotide sequence of the 133rd to 825th nucleotides set forth in SEQ ID NO: 2;
a DNA consisting of the nucleotide sequence of the 163rd to 825th nucleotides set forth in SEQ ID NO: 2;
a DNA consisting of the nucleotide sequence of the 193rd to 825th nucleotides set forth in SEQ ID NO: 2;
a DNA consisting of the nucleotide sequence of the 223rd to 825th nucleotides set forth in SEQ ID NO: 2;
a DNA consisting of the nucleotide sequence of the 253rd to 825th nucleotides set forth in SEQ ID NO: 2;
a DNA consisting of the nucleotide sequence of the 283rd to 825th nucleotides set forth in SEQ ID NO: 2;
a DNA consisting of the nucleotide sequence of the 313rd to 825th nucleotides set forth in SEQ ID NO: 2; and
a DNA having any one of these nucleotide sequences, in which 1 or more and 20 or less nucleotides are mutated, and encoding a protein having acyl-ACP thioesterase activity.

16. The method according to claim 13, wherein the host is a microalga.

* * * * *